United States Patent
McGuckin, Jr. et al.

(10) Patent No.: US 7,390,322 B2
(45) Date of Patent: *Jun. 24, 2008

(54) DIALYSIS CATHETER AND METHODS OF INSERTION

(75) Inventors: James F. McGuckin, Jr., Radnor, PA (US); Paul Tashjian, King of Prussia, PA (US); Michael W. Paris, Hatfield, PA (US); Peter W. J. Hinchliffe, Downington, PA (US)

(73) Assignee: Rex Medical, L.P., Conshohocken, PA (US)

( * ) Notice: Subject to any disclaimer, the term of this patent is extended or adjusted under 35 U.S.C. 154(b) by 304 days.

This patent is subject to a terminal disclaimer.

(21) Appl. No.: 10/939,102

(22) Filed: Sep. 10, 2004

(65) Prior Publication Data

US 2005/0090776 A1    Apr. 28, 2005

Related U.S. Application Data

(63) Continuation of application No. 10/025,505, filed on Dec. 19, 2001, now Pat. No. 6,858,019.

(60) Provisional application No. 60/260,592, filed on Jan. 9, 2001.

(51) Int. Cl.
*A61M 31/00* (2006.01)
(52) U.S. Cl. .......................... 604/500; 604/508; 604/510
(58) Field of Classification Search ................... 604/43, 604/500, 507, 508, 514, 523, 524, 29, 264, 604/104, 105, 107, 510
See application file for complete search history.

(56) References Cited

U.S. PATENT DOCUMENTS

| 1,248,492 A | 12/1917 | Hill |
| 2,024,982 A | 12/1935 | Scott |

(Continued)

FOREIGN PATENT DOCUMENTS

| EP | 0301854 | 2/1989 |
| EP | 0440992 | 8/1991 |
| WO | WO 9737699 | 10/1997 |
| WO | WO 0176677 | 10/2001 |

OTHER PUBLICATIONS

Moureau, Modified Seldinger Insertion Technique for PICC Insertion: The New Wave for Nurses. Seldinger Technique for Introducing Catheters.
Journal of Vascular and Interventional Radiology 12:376-378 (2001), Sheathless Technique of Ash Split-Cath Insertion, Aalpen Patel, MD; Stephen Hofkin, MD; David Ball, DO; Gary Cohen, MD and Douglas C. Smith MD.

*Primary Examiner*—Kevin C. Sirmons
*Assistant Examiner*—Bhisma Mehta
(74) *Attorney, Agent, or Firm*—Neil D. Gershon

(57) ABSTRACT

A method of inserting a dialysis catheter into a patient comprising the steps of inserting a guidewire into the jugular vein of the patient through the superior vena cava and into the inferior vena cava, providing a trocar having a lumen and a dissecting tip, inserting the trocar to enter an incision in the patient and to create a subcutaneous tissue tunnel, threading the guidewire through the lumen of the trocar so the guidewire extends through the incision, providing a dialysis catheter having first and second lumens, removing the trocar, and inserting the dialysis catheter over the guidewire through the incision and through the jugular vein and superior vena cava into the right atrium.

21 Claims, 26 Drawing Sheets

U.S. PATENT DOCUMENTS

| | | |
|---|---|---|
| 2,460,473 A | 2/1949 | Larkin et al. |
| 3,336,927 A | 8/1967 | Klebanoff |
| 3,680,562 A | 8/1972 | Wittes et al. |
| 3,833,003 A | 9/1974 | Taricco |
| 3,938,530 A | 2/1976 | Santomieri |
| 4,134,402 A | 1/1979 | Mahurkar |
| 4,270,535 A | 6/1981 | Bogue et al. |
| 4,299,228 A | 11/1981 | Peters |
| 4,345,602 A | 8/1982 | Yoshimura |
| 4,403,983 A | 9/1983 | Edelman et al. |
| 4,406,656 A | 9/1983 | Hattler et al. |
| 4,431,426 A | 2/1984 | Groshong et al. |
| 4,432,752 A | 2/1984 | Marion |
| 4,451,252 A | 5/1984 | Martin |
| 4,479,792 A | 10/1984 | Lazarus et al. |
| 4,490,136 A | 12/1984 | Ekblahd et al. |
| 4,493,696 A | 1/1985 | Uldall |
| 4,543,087 A | 9/1985 | Sommercorn et al. |
| 4,545,373 A | 10/1985 | Christoudias |
| 4,568,329 A | 2/1986 | Mahurkar |
| 4,574,806 A | 3/1986 | McCarthy |
| 4,581,012 A | 4/1986 | Brown et al. |
| 4,583,968 A | 4/1986 | Mahurkar |
| 4,619,643 A | 10/1986 | Bai |
| 4,623,327 A | 11/1986 | Mahurkar |
| 4,643,711 A | 2/1987 | Bates |
| 4,668,221 A | 5/1987 | Luther |
| 4,670,009 A | 6/1987 | Bullock |
| 4,682,978 A | 7/1987 | Martin |
| 4,717,379 A | 1/1988 | Ekholmer |
| 4,738,667 A | 4/1988 | Galloway |
| 4,769,016 A | 9/1988 | Labianca |
| 4,776,841 A | 10/1988 | Catalano |
| 4,808,155 A | 2/1989 | Mahurkar |
| 4,808,163 A | 2/1989 | Laub |
| 4,832,687 A | 5/1989 | Smith |
| 4,842,582 A | 6/1989 | Mahurkar |
| 4,846,804 A | 7/1989 | Davis et al. |
| 4,894,057 A | 1/1990 | Howes |
| 4,895,561 A | 1/1990 | Mahurkar |
| 4,927,418 A | 5/1990 | Dake et al. |
| 4,950,259 A | 8/1990 | Geary et al. |
| 4,961,809 A | 10/1990 | Martin |
| 4,968,307 A | 11/1990 | Dake et al. |
| 4,994,027 A | 2/1991 | Farrell |
| 5,009,636 A | 4/1991 | Wortley et al. |
| 5,021,044 A | 6/1991 | Sharkawy |
| 5,053,004 A | 10/1991 | Markel et al. |
| 5,053,023 A | 10/1991 | Martin |
| 5,057,073 A | 10/1991 | Martin |
| 5,057,075 A | 10/1991 | Moncrief et al. |
| 5,059,170 A | 10/1991 | Cameron |
| 5,098,413 A | 3/1992 | Trudell et al. |
| 5,122,125 A | 6/1992 | Deuss |
| 5,135,599 A | 8/1992 | Martin et al. |
| 5,139,486 A | 8/1992 | Moss |
| 5,156,592 A | 10/1992 | Martin et al. |
| 5,167,623 A | 12/1992 | Cianci et al. |
| 5,171,216 A | 12/1992 | Dasse et al. |
| 5,195,962 A | 3/1993 | Martin et al. |
| 5,207,648 A | 5/1993 | Gross |
| 5,207,650 A | 5/1993 | Martin |
| 5,209,723 A | 5/1993 | Twardowski et al. |
| 5,209,742 A | 5/1993 | Venema et al. |
| 5,213,111 A | 5/1993 | Cook |
| 5,215,527 A | 6/1993 | Beck et al. |
| 5,221,255 A | 6/1993 | Mahurkar et al. |
| 5,221,256 A | 6/1993 | Mahurkar |
| 5,234,438 A | 8/1993 | Semrad |
| 5,246,430 A | 9/1993 | MacFarlane |
| 5,273,527 A | 12/1993 | Schatz et al. |
| 5,279,596 A | 1/1994 | Castaneda et al. |
| 5,338,293 A | 8/1994 | Jeppsson et al. |
| 5,346,471 A | 9/1994 | Raulserson |
| 5,348,536 A | 9/1994 | Young et al. |
| 5,350,358 A | 9/1994 | Martin |
| 5,360,397 A | 11/1994 | Pinchuk |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,380,290 A | 1/1995 | Makower et al. |
| 5,382,238 A * | 1/1995 | Abrahamson et al. .. 604/170.01 |
| 5,395,316 A | 3/1995 | Martin |
| 5,403,291 A | 4/1995 | Abrahamson |
| 5,405,320 A | 4/1995 | Twardowski et al. |
| 5,405,341 A | 4/1995 | Martin |
| 5,431,661 A | 7/1995 | Koch |
| 5,451,206 A | 9/1995 | Young |
| 5,468,159 A | 11/1995 | Brodsky |
| 5,472,417 A | 12/1995 | Martin et al. |
| 5,480,380 A | 1/1996 | Martin |
| 5,486,159 A | 1/1996 | Mahurkar |
| 5,489,278 A | 2/1996 | Abrahamson |
| 5,509,897 A | 4/1996 | Twardowski et al. |
| 5,509,900 A | 4/1996 | Kirkman |
| 5,542,925 A | 8/1996 | Orth |
| 5,556,390 A | 9/1996 | Hicks |
| 5,569,182 A | 10/1996 | Twardowski et al. |
| 5,571,093 A | 11/1996 | Cruz et al. |
| 5,662,606 A | 9/1997 | Cimino et al. |
| 5,693,030 A | 12/1997 | Lee et al. |
| 5,713,849 A | 2/1998 | Bosma et al. |
| 5,718,678 A | 2/1998 | Fleming, III |
| 5,752,939 A | 5/1998 | Makoto |
| 5,792,123 A | 8/1998 | Ensminger |
| 5,797,869 A | 8/1998 | Leblanc et al. |
| 5,807,311 A | 9/1998 | Palestrant |
| 5,807,329 A | 9/1998 | Gelman |
| 5,810,789 A | 9/1998 | Powers et al. |
| 5,830,196 A | 11/1998 | Hicks |
| 5,882,347 A | 3/1999 | Mouris-Laan et al. |
| 5,911,715 A | 6/1999 | Berg et al. |
| 5,913,848 A | 6/1999 | Luther et al. |
| 5,916,208 A | 6/1999 | Luther et al. |
| 5,919,160 A | 7/1999 | Sanfilippo |
| 5,944,732 A | 8/1999 | Raulerson et al. |
| 5,947,953 A | 9/1999 | Ash et al. |
| 5,957,893 A | 9/1999 | Luther et al. |
| 5,961,486 A | 10/1999 | Twardowski et al. |
| 5,976,103 A | 11/1999 | Martin |
| 5,976,120 A | 11/1999 | Chow et al. |
| 5,984,908 A | 11/1999 | Davis et al. |
| 5,989,206 A | 11/1999 | Prosl et al. |
| 6,001,079 A | 12/1999 | Pourchez |
| 6,036,654 A | 3/2000 | Quinn et al. |
| 6,059,771 A | 5/2000 | Balbierz et al. |
| 6,106,540 A | 8/2000 | White et al. |
| 6,120,494 A | 9/2000 | Jonkman |
| 6,126,631 A | 10/2000 | Loggie |
| 6,132,405 A | 10/2000 | Nilsson et al. |
| 6,146,354 A | 11/2000 | Beil |
| 6,146,373 A | 11/2000 | Cragg et al. |
| 6,152,909 A | 11/2000 | Bagaoisan et al. |
| 6,156,016 A | 12/2000 | Maginot |
| 6,180,059 B1 | 1/2001 | Divino, Jr. et al. |
| 6,190,349 B1 | 2/2001 | Ash et al. |
| 6,190,371 B1 | 2/2001 | Maginot et al. |
| 6,193,685 B1 | 2/2001 | Goodin |
| 6,196,996 B1 | 3/2001 | Teirstein |
| 6,210,365 B1 | 4/2001 | Afzal |
| 6,223,070 B1 | 4/2001 | Chait |
| 6,264,627 B1 | 7/2001 | Liska et al. |
| 6,273,879 B1 | 8/2001 | Keith et al. |

| | | | | | | |
|---|---|---|---|---|---|---|
| 6,280,423 | B1 | 8/2001 | Davey et al. | 6,858,019 B2 * | 2/2005 | McGuckin et al. ............ 604/43 |
| 6,293,927 | B1 | 9/2001 | McGuckin, Jr. | 6,890,321 B2 | 5/2005 | Luther et al. |
| 6,293,958 | B1 | 9/2001 | Berry et al. | 7,204,831 B2 * | 4/2007 | McGuckin et al. .......... 604/510 |
| 6,296,631 | B2 | 10/2001 | Chow | 2002/0055714 A1 * | 5/2002 | Rothschild ............... 604/164.1 |
| 6,328,730 | B1 | 12/2001 | Harkrider, Jr. | 2002/0087145 A1 | 7/2002 | Ehwald et al. |
| 6,358,229 | B1 | 3/2002 | Tihon | 2003/0023198 A1 | 1/2003 | Twardowski |
| 6,361,529 | B1 | 3/2002 | Goodin et al. | 2003/0088213 A1 | 5/2003 | Schweikert et al. |
| 6,394,141 | B2 | 5/2002 | Wages et al. | 2003/0153898 A1 | 8/2003 | Schon et al. |
| 6,454,997 | B1 | 9/2002 | Divino, Jr. et al. | 2003/0204179 A1 | 10/2003 | Davey et al. |
| 6,638,242 | B2 | 10/2003 | Wilson et al. | 2004/0064086 A1 | 4/2004 | Gottlieb et al. |
| 6,786,884 | B1 | 9/2004 | DeCant, Jr. et al. | 2006/0259007 A1 * | 11/2006 | McGuckin et al. .......... 604/506 |
| 6,827,710 | B1 | 12/2004 | Mooney et al. | | | |

* cited by examiner

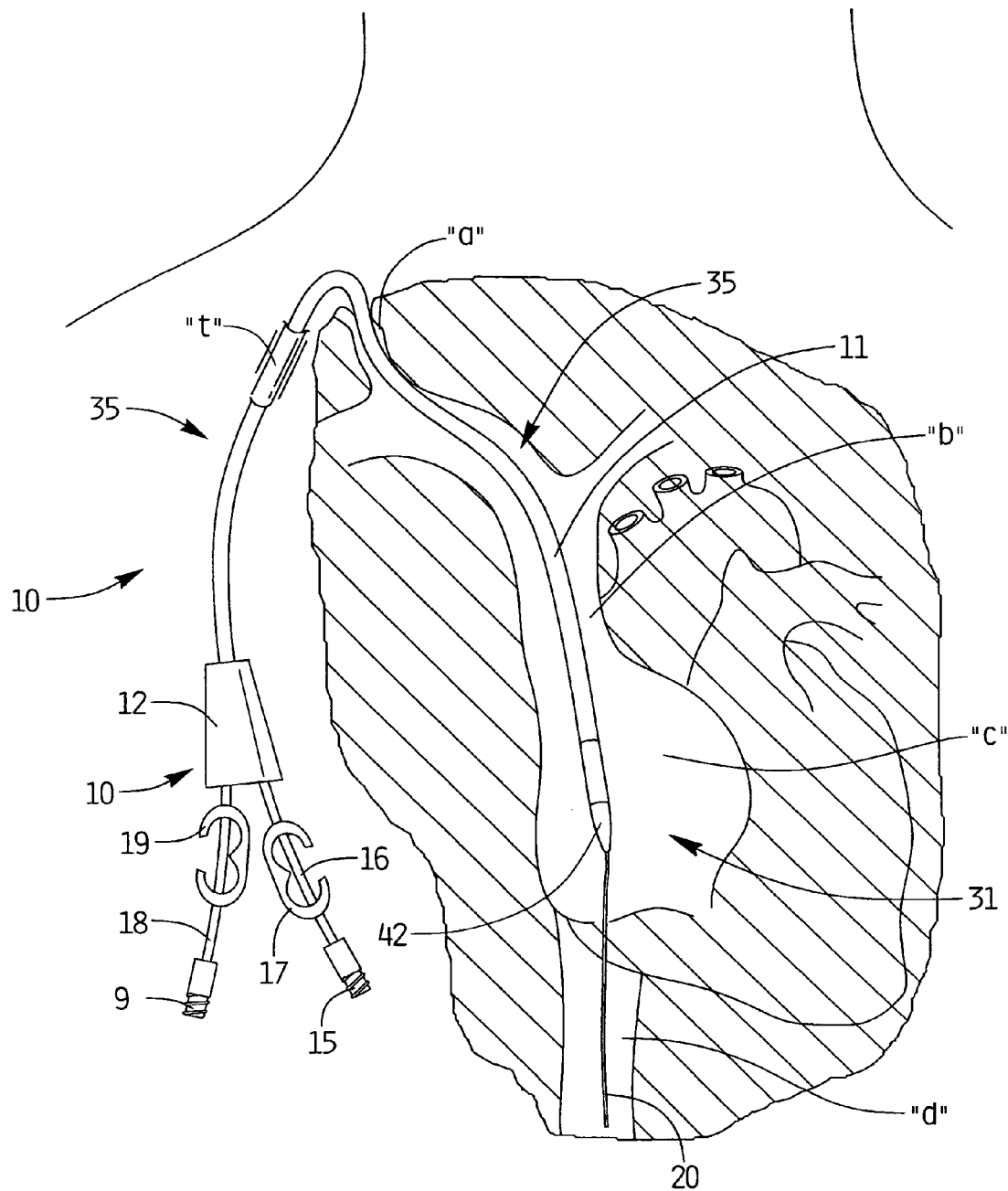
FIG_1

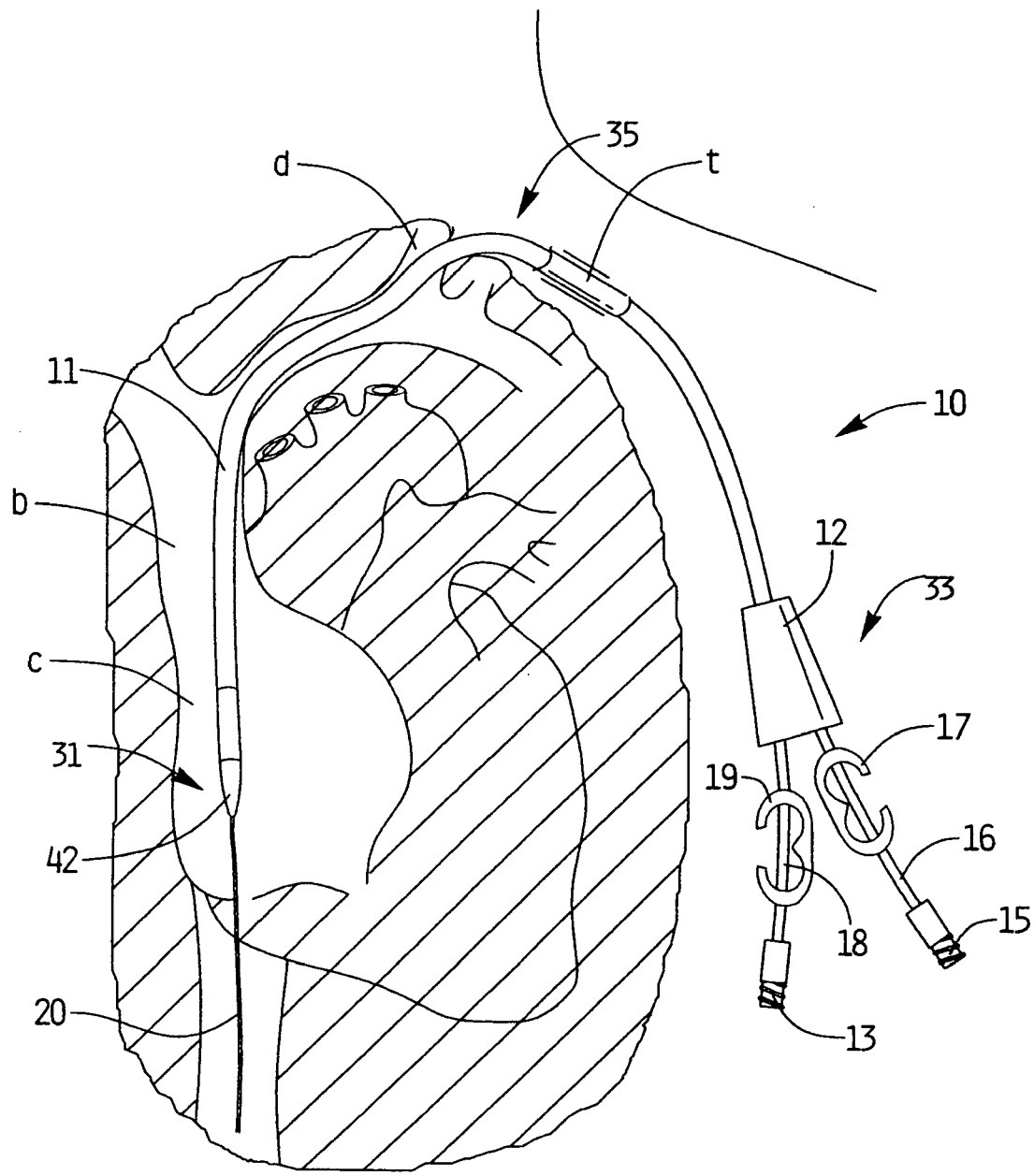
FIG_2

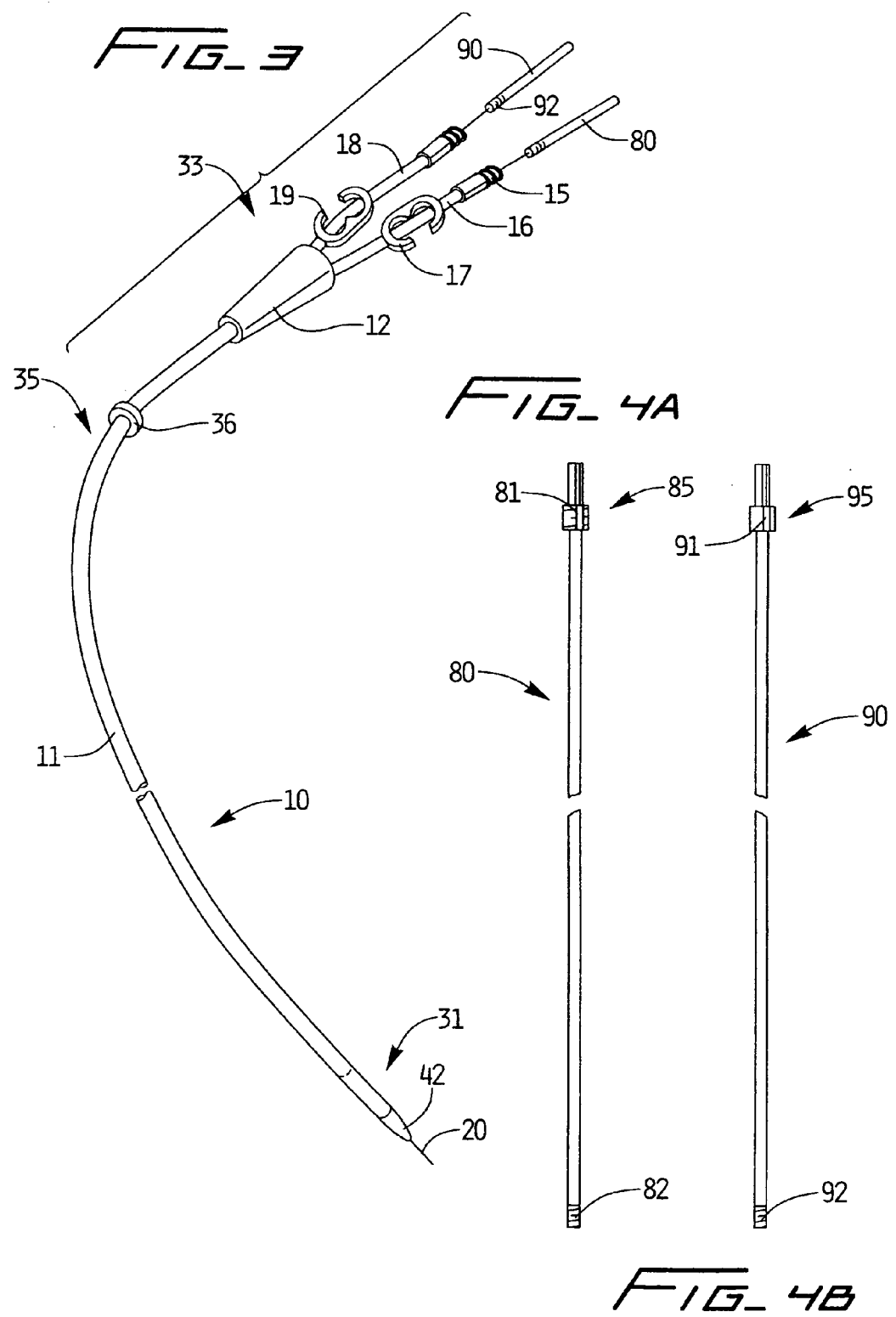

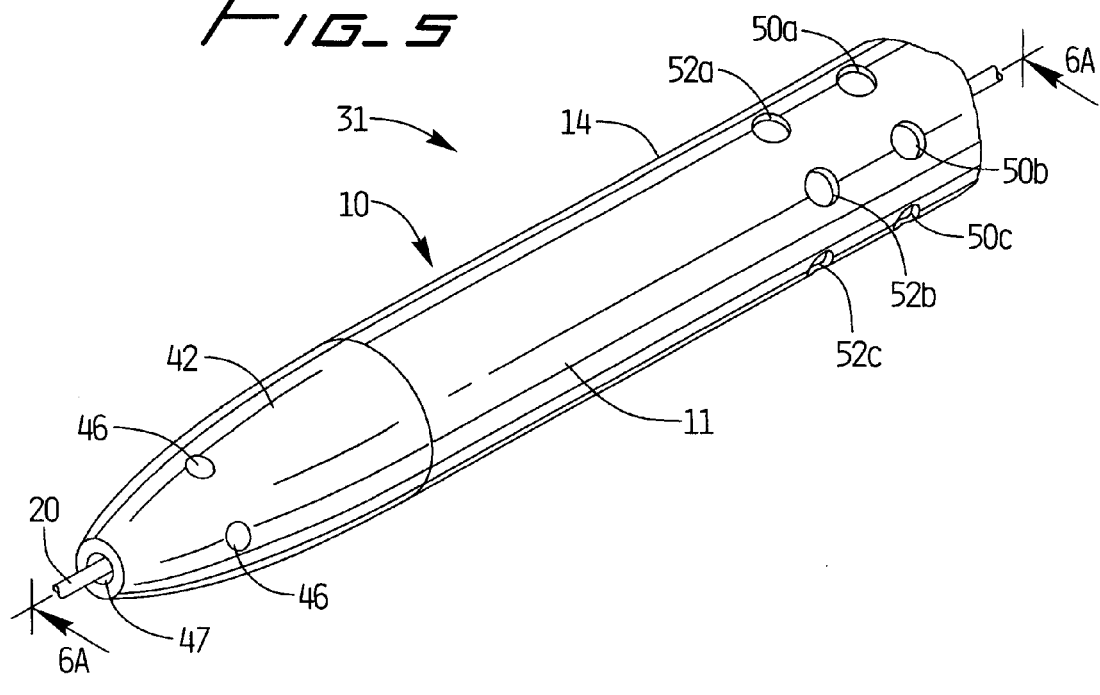
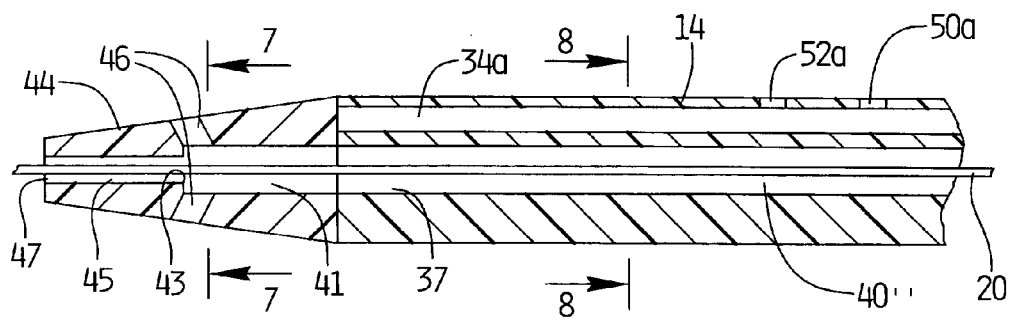
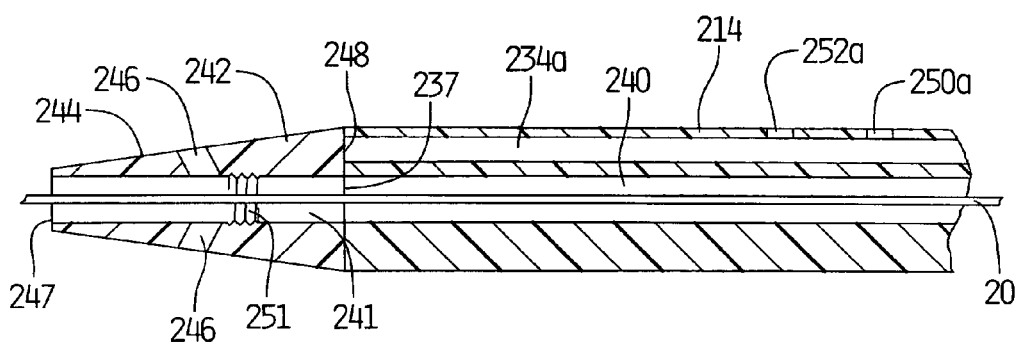

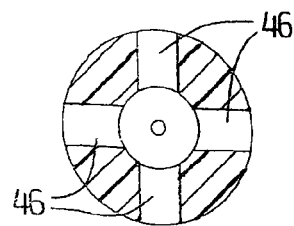
FIG_7
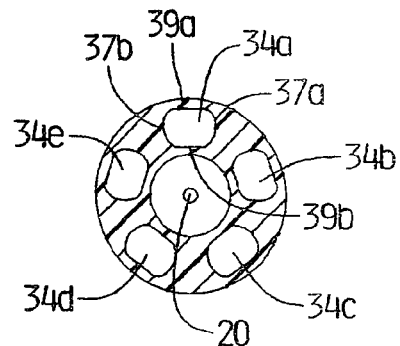
FIG_8
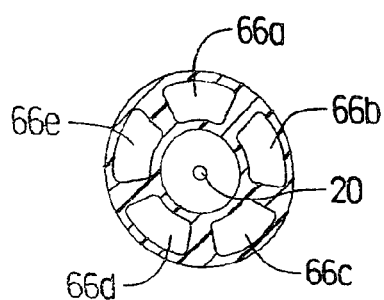
FIG_9A
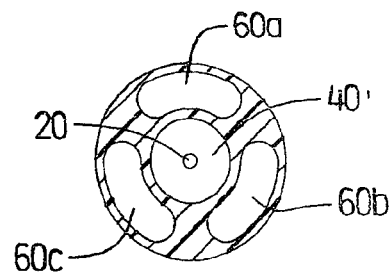
FIG_9B
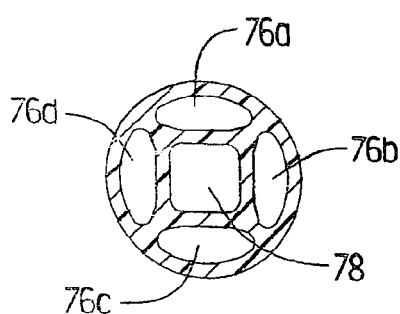
FIG_9C
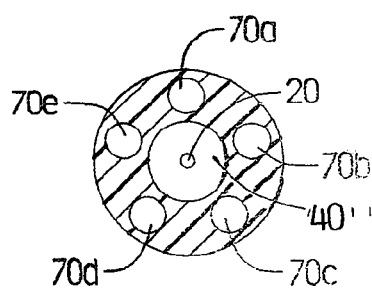
FIG_10

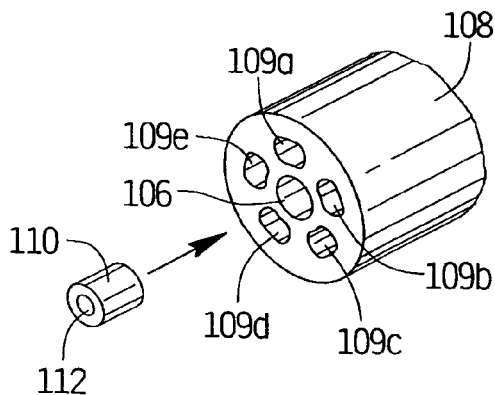
FIG_13A
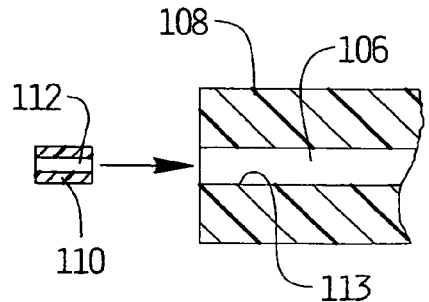
FIG_13B
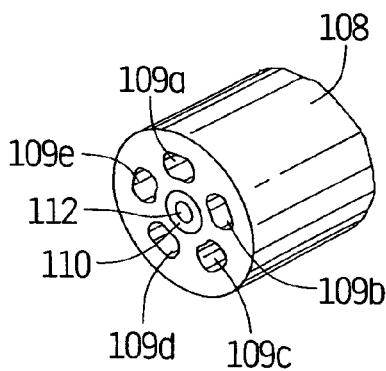
FIG_14A
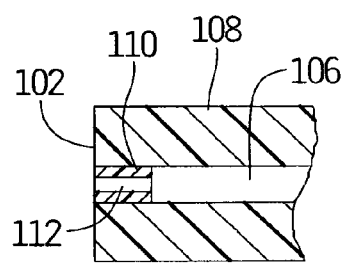
FIG_14B
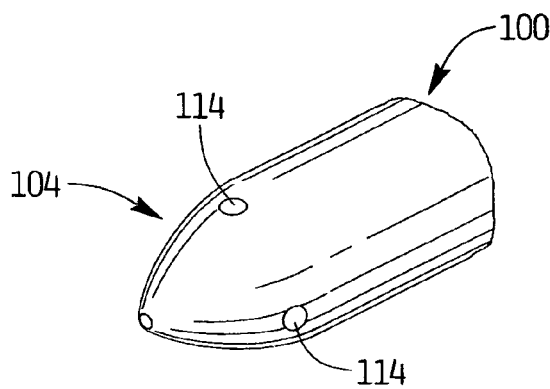
FIG_15A
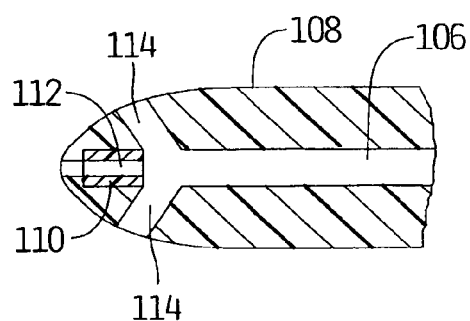
FIG_15B

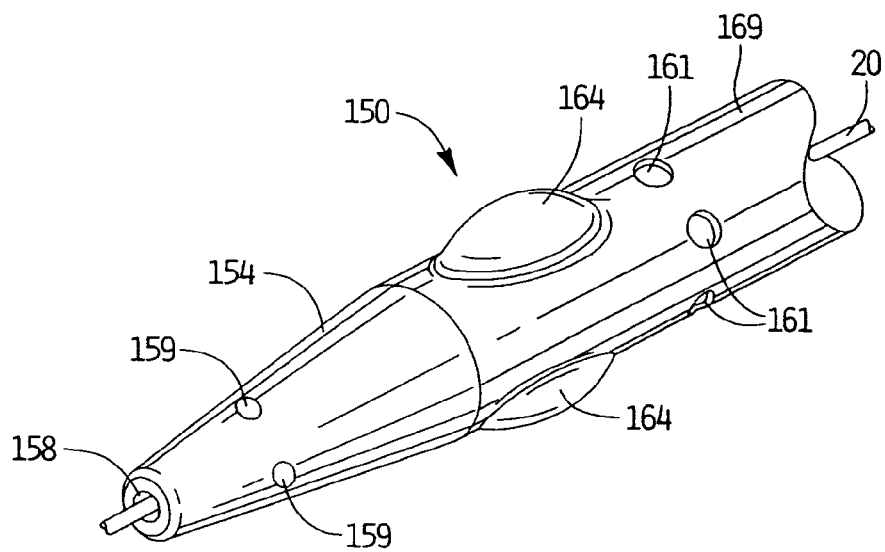
FIG_16A
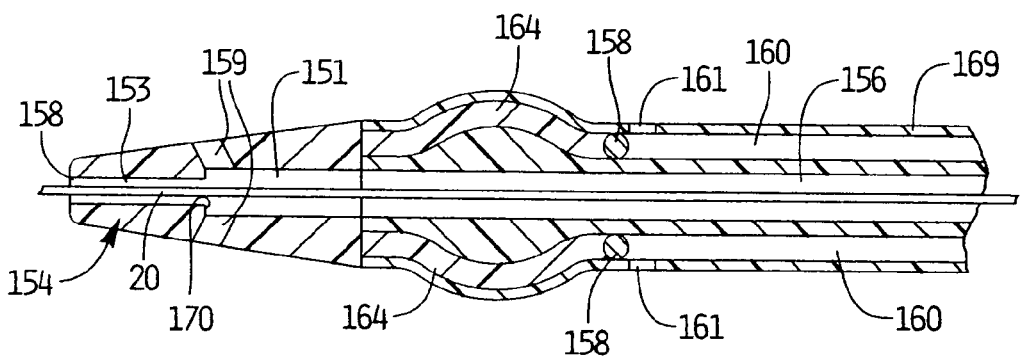
FIG_16B
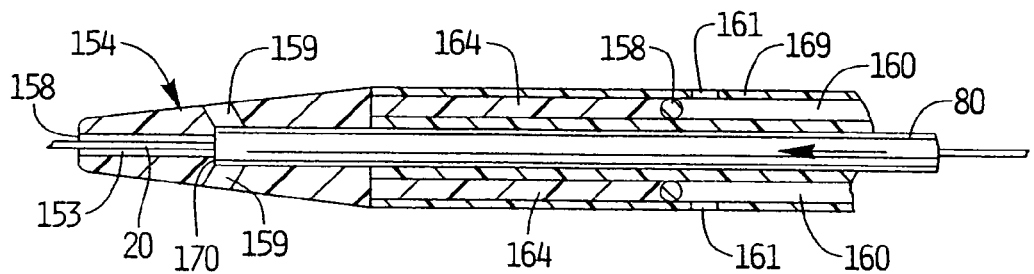
FIG_16C

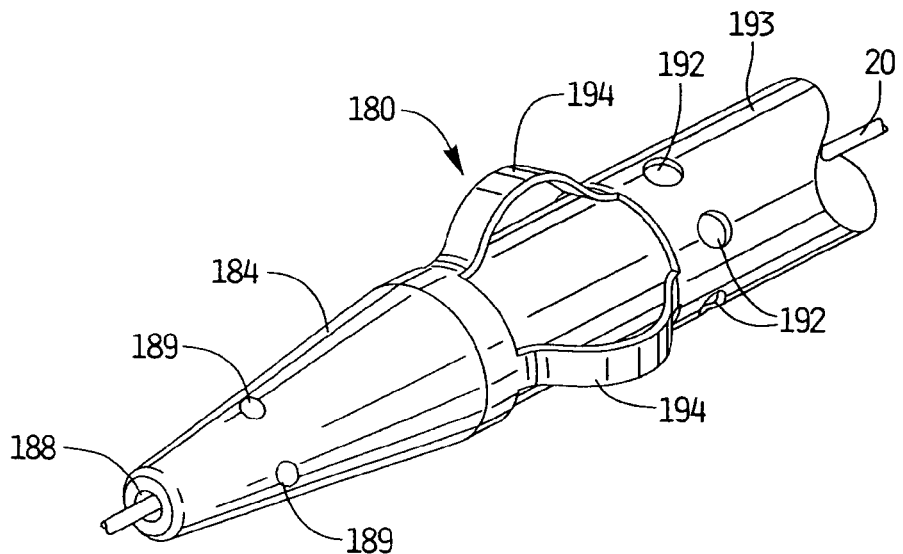
FIG_17A
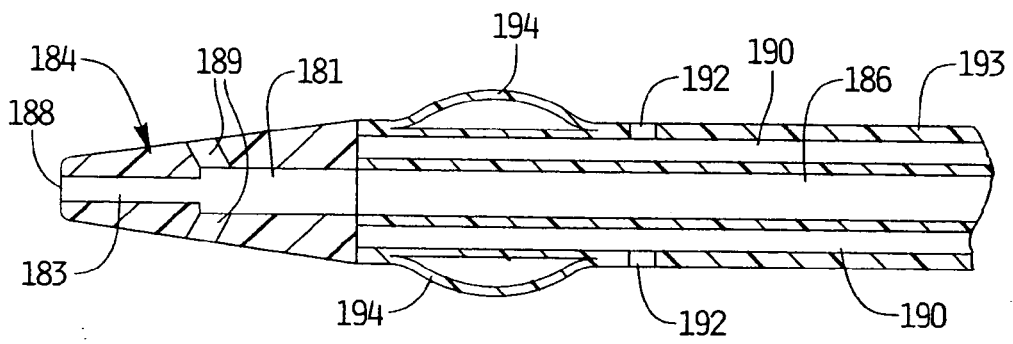
FIG_17B
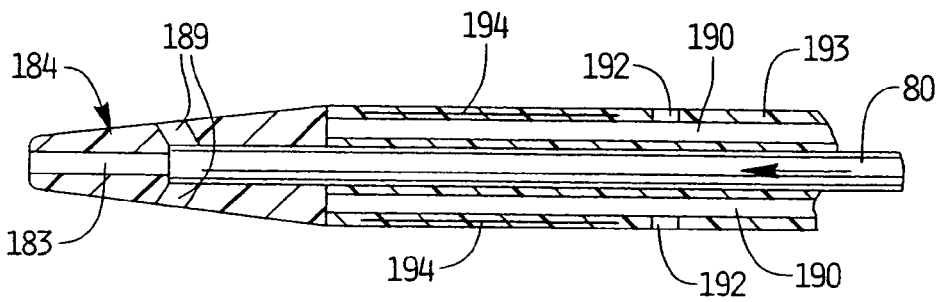
FIG_17C

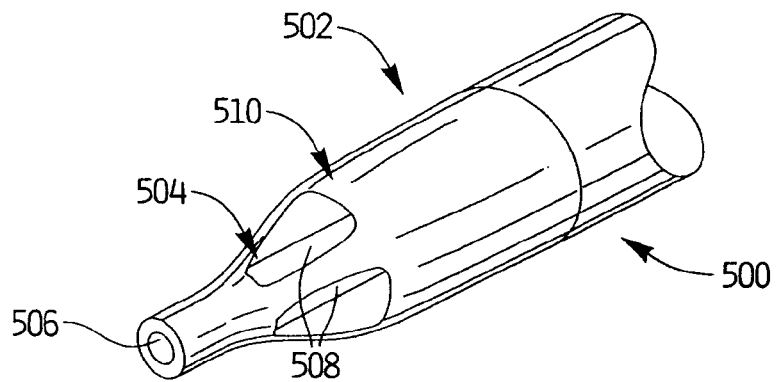
FIG_18
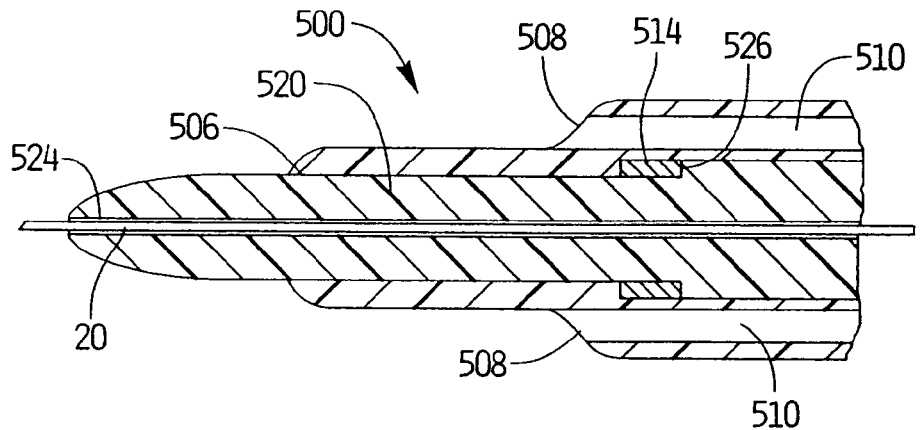
FIG_19
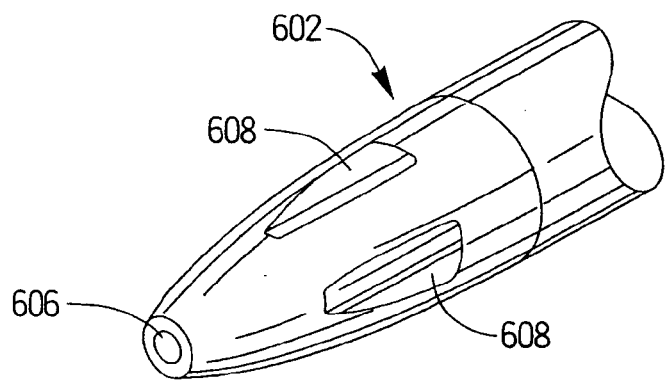
FIG_20

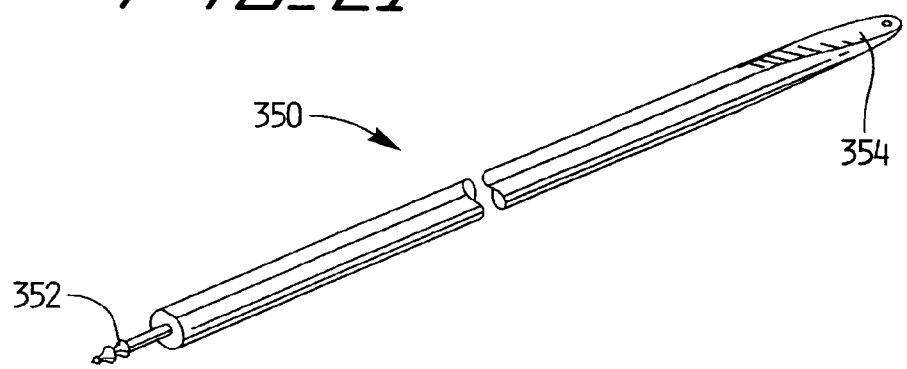
FIG_21
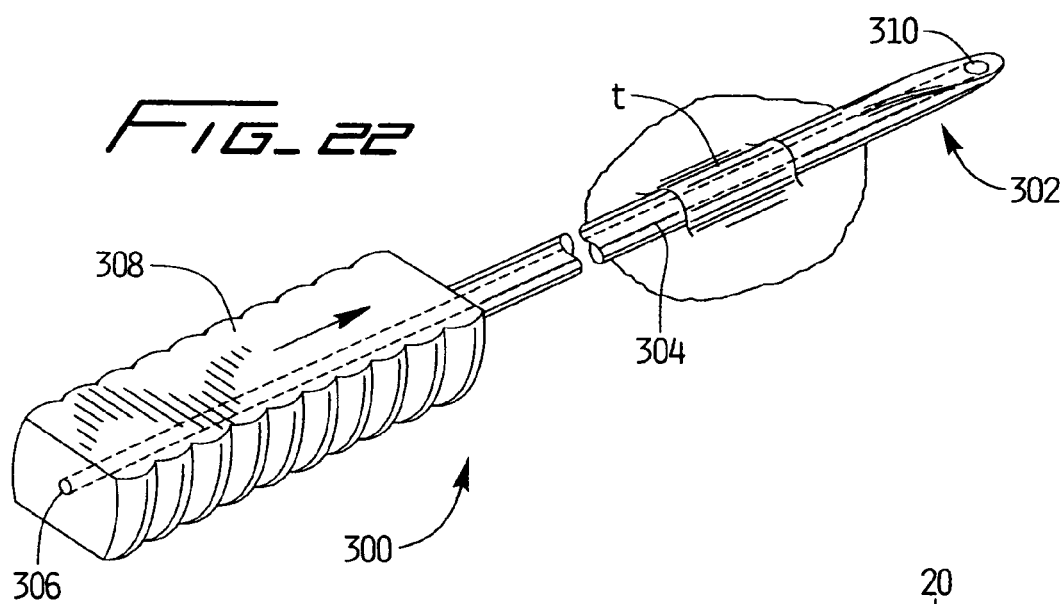
FIG_22
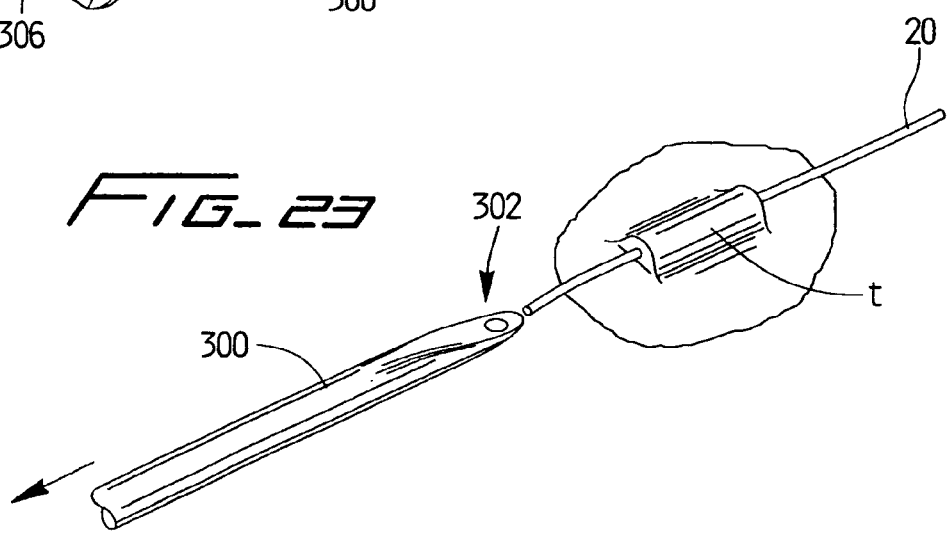
FIG_23

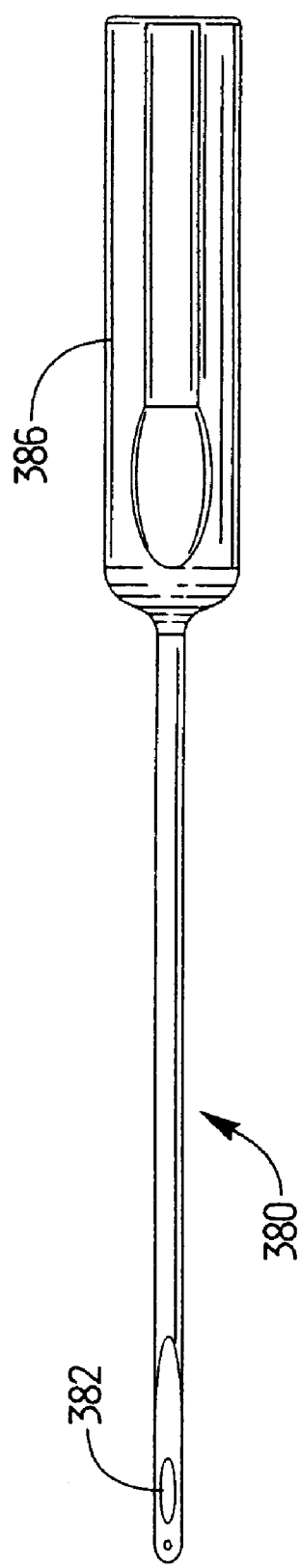
FIG._24A
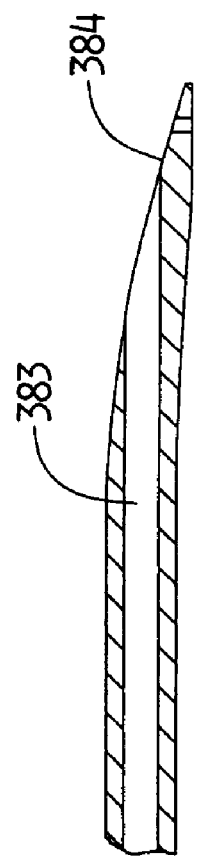
FIG._24B

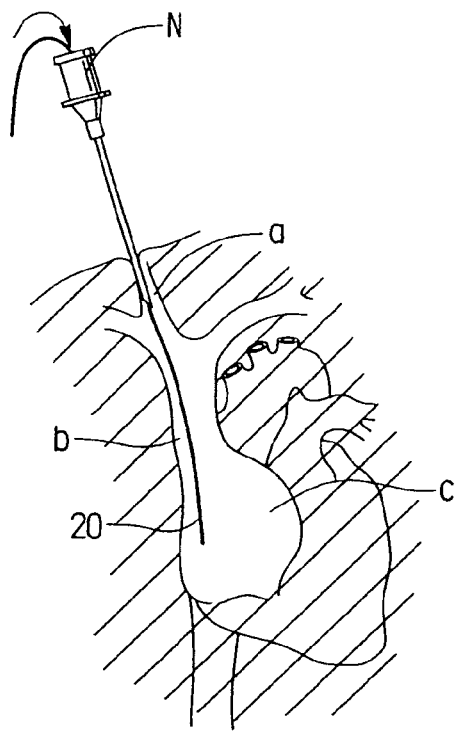
FIG_25
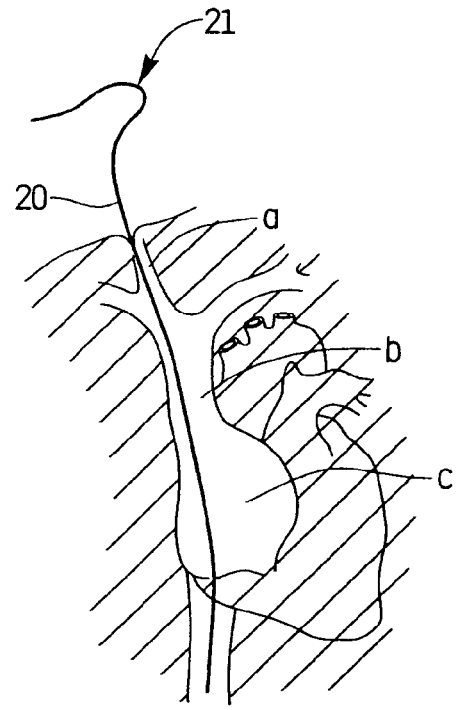
FIG_26
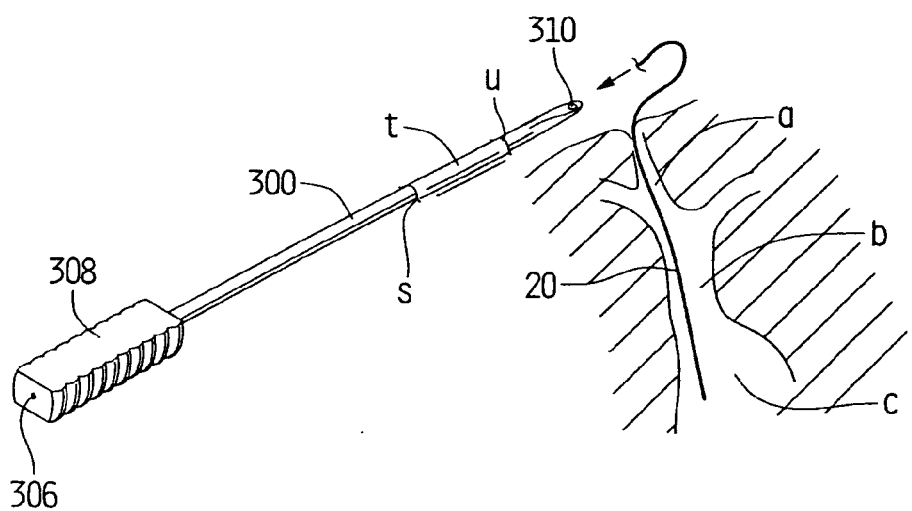
FIG_27

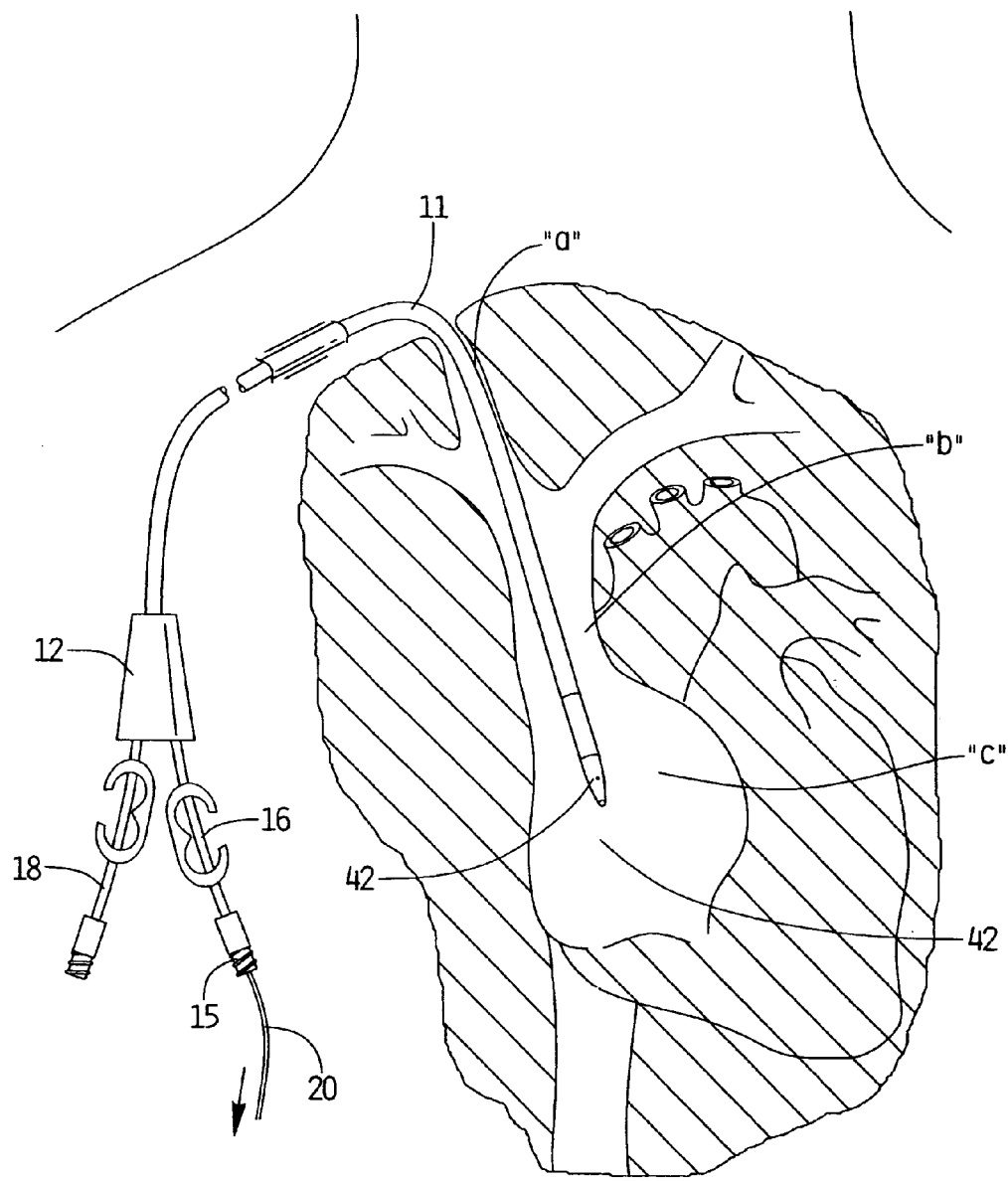
FIG_28C

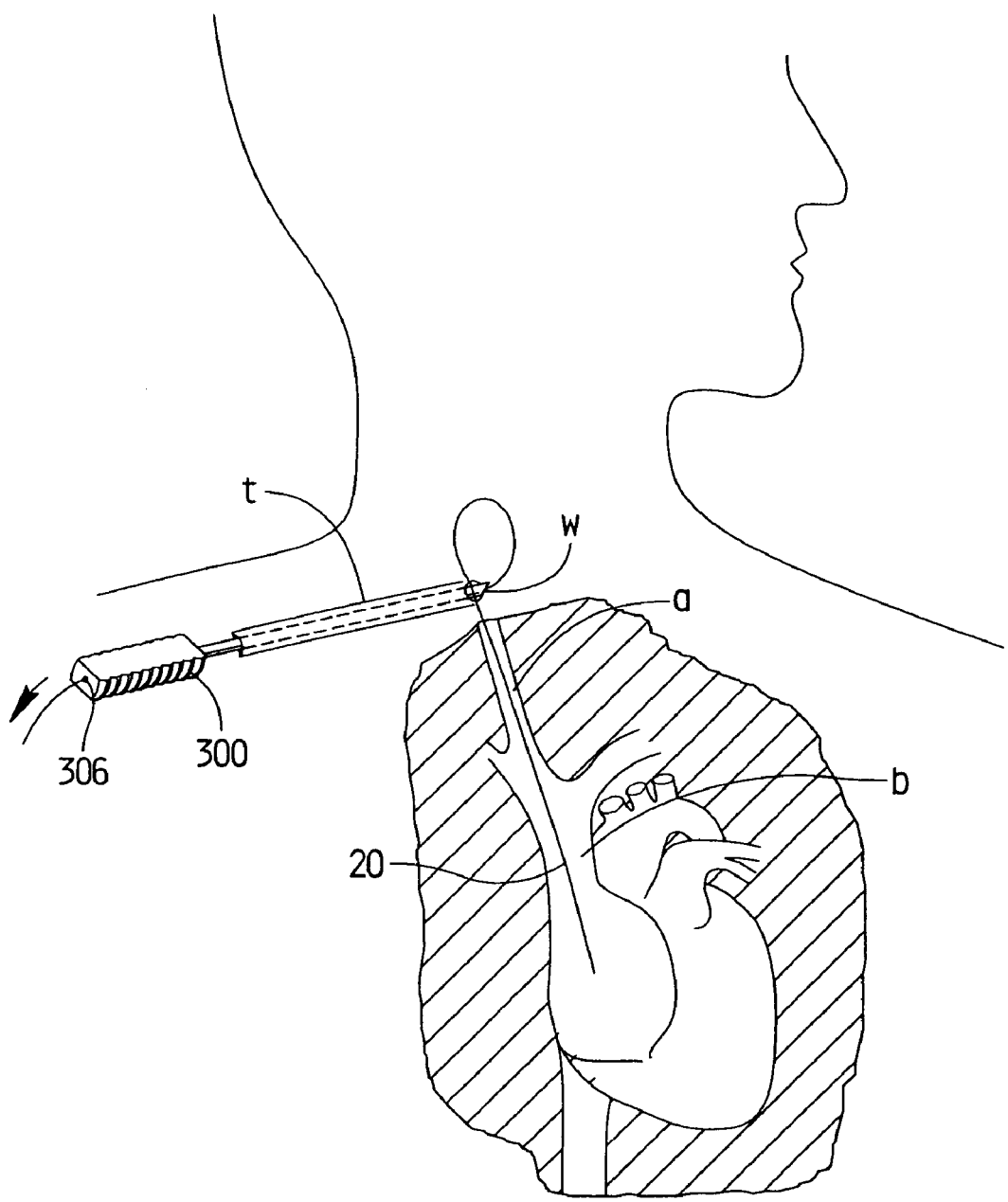
FIG_29A

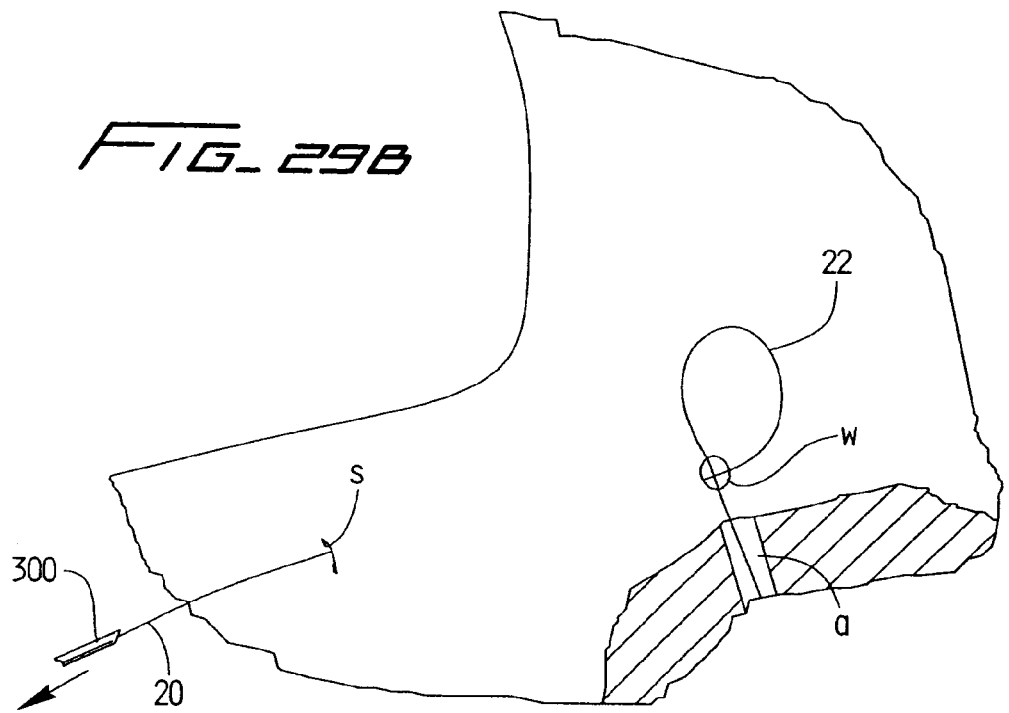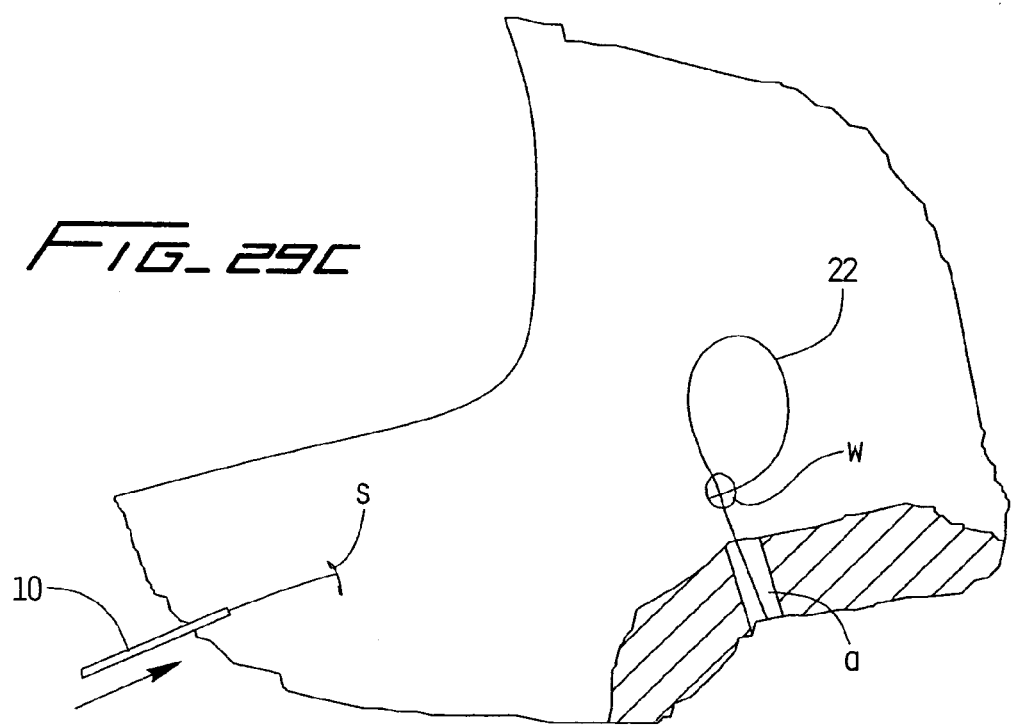

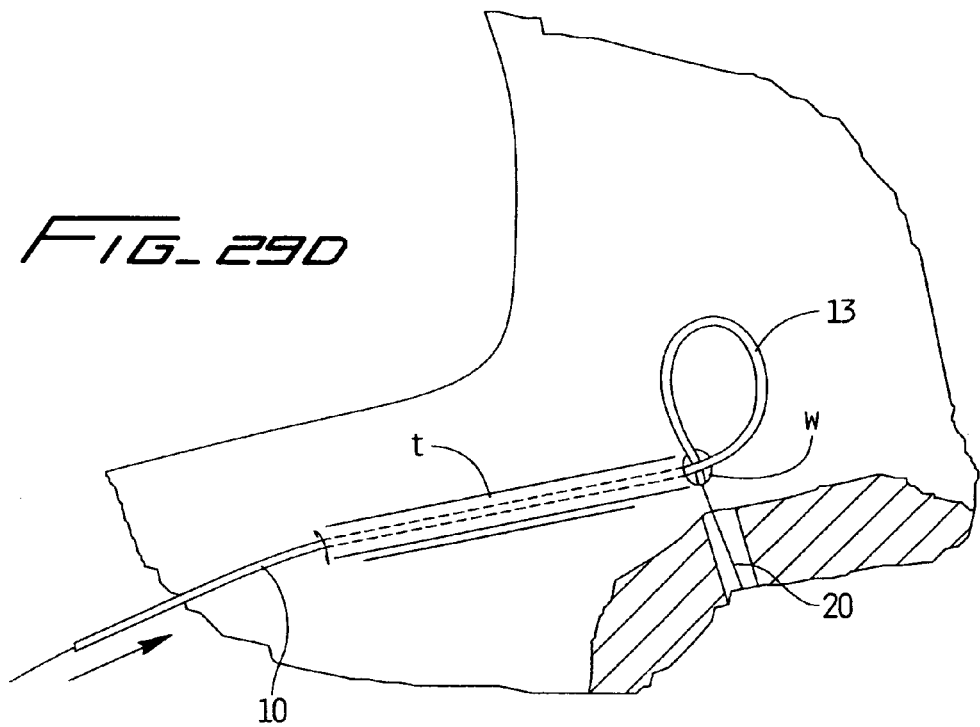
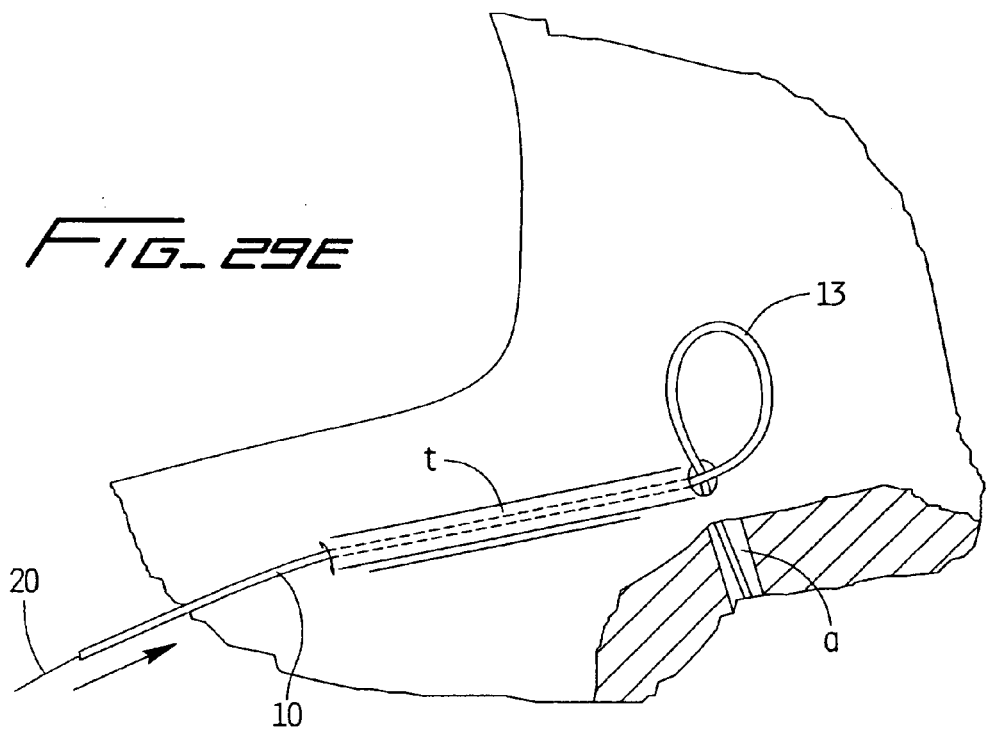

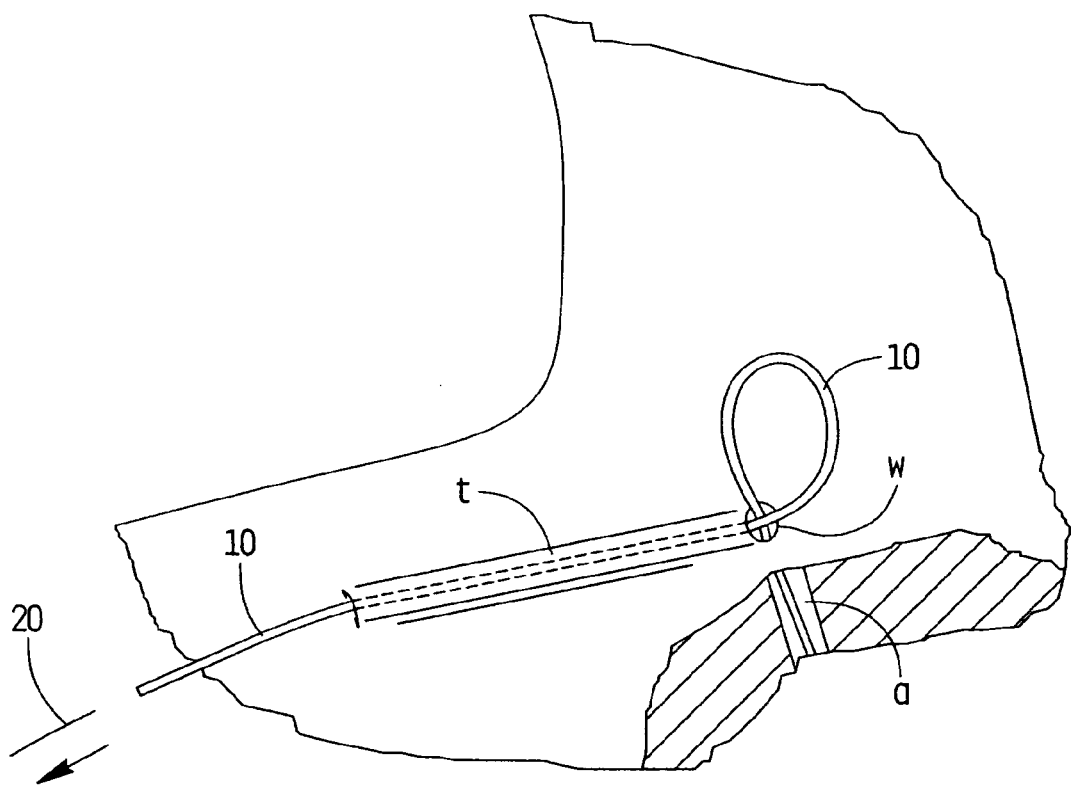
FIG_29F

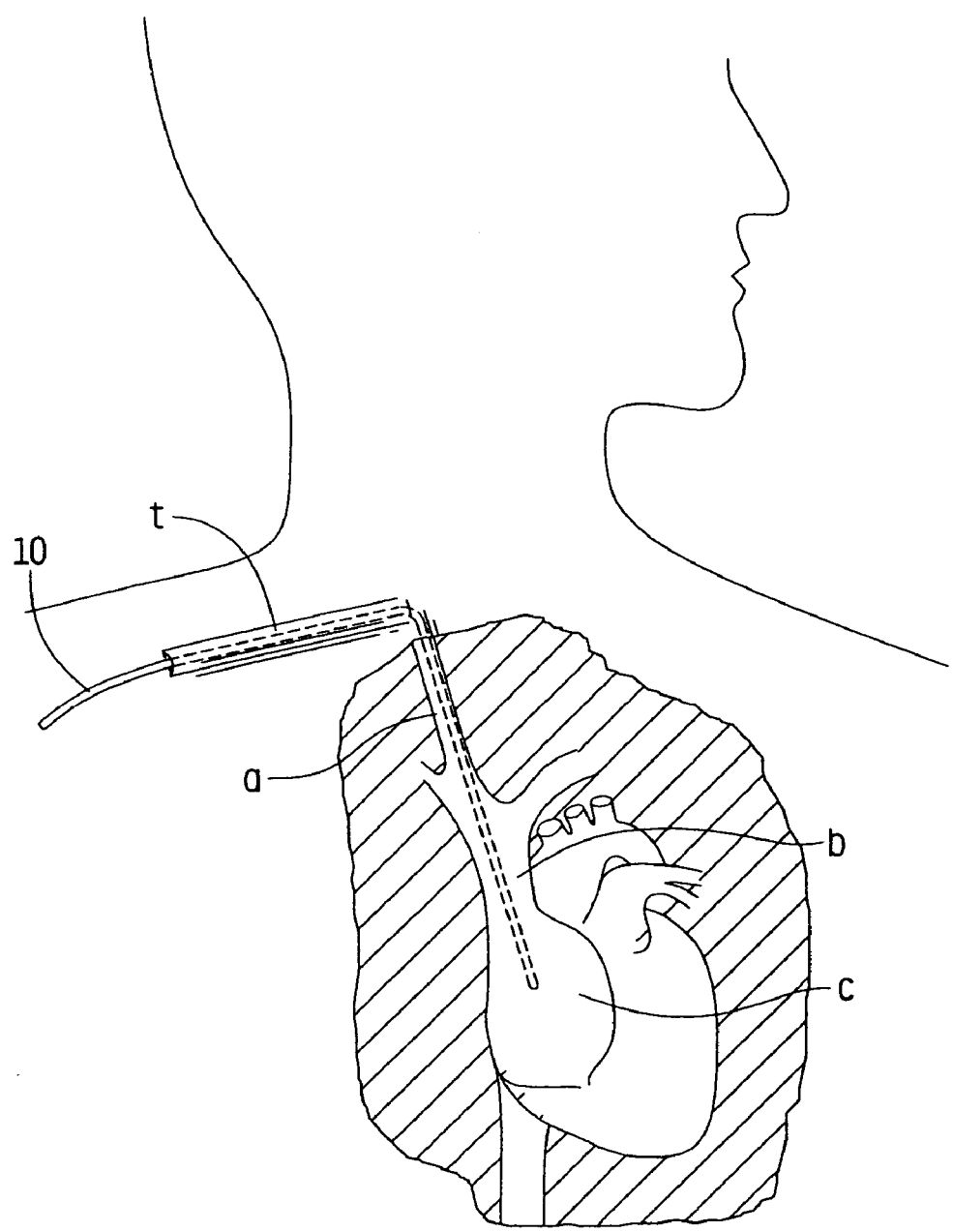
FIG_29G

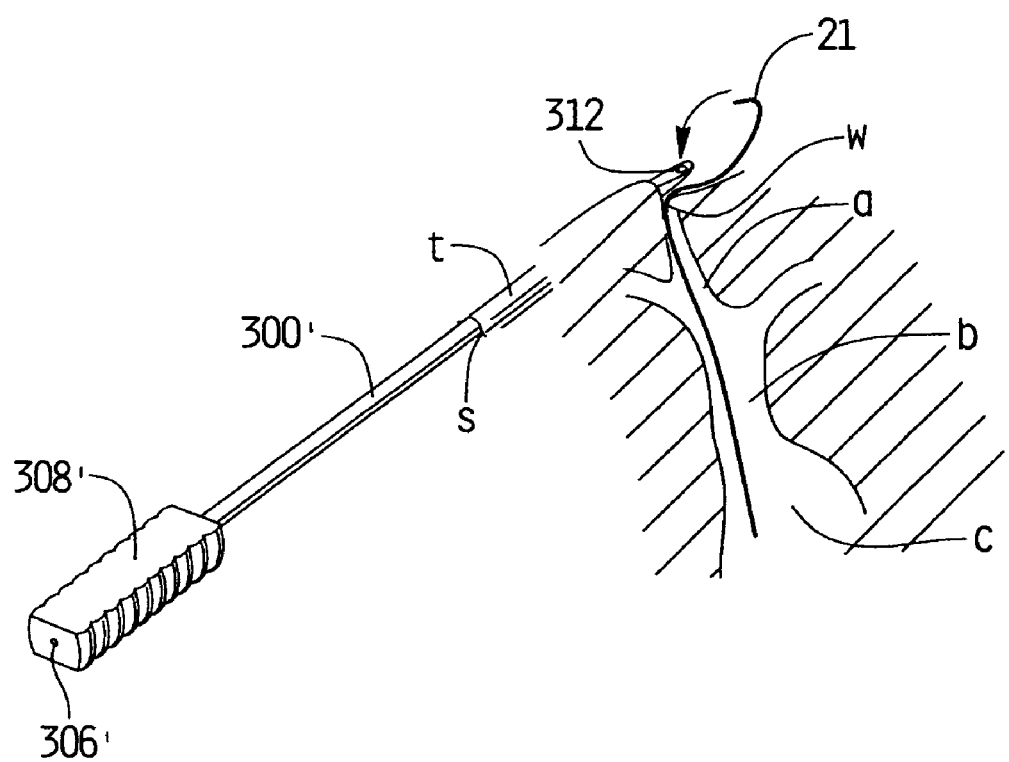
FIG_30

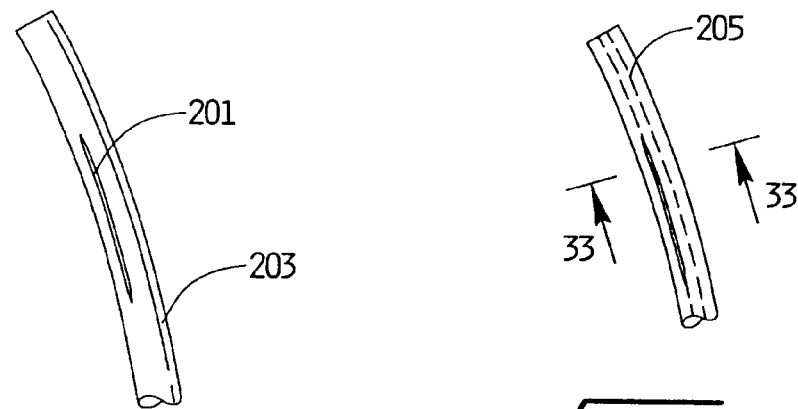
FIG_31   FIG_32
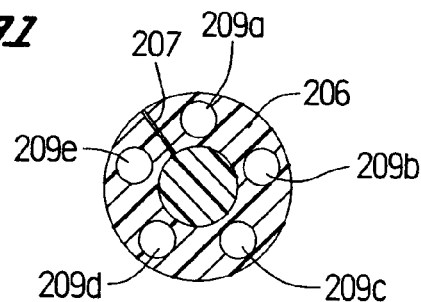
FIG_33
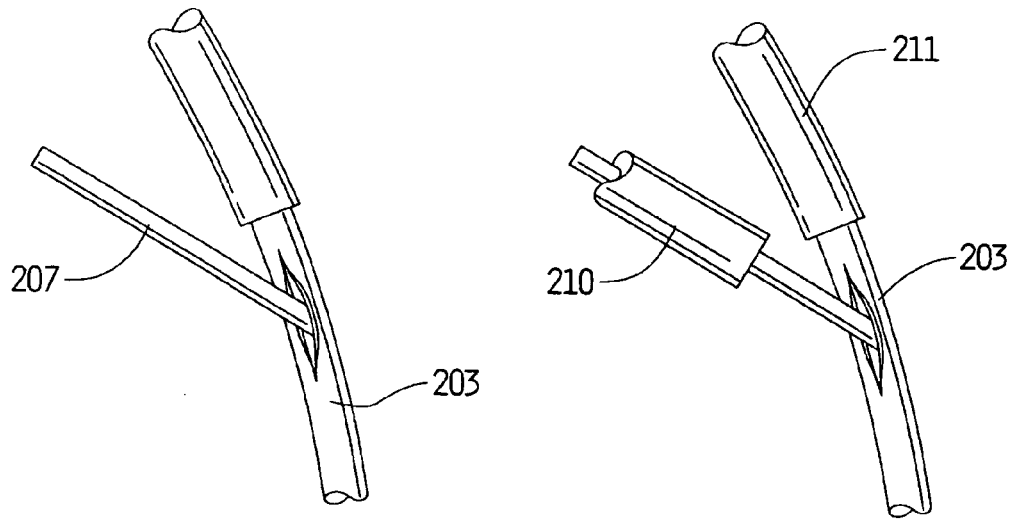
FIG_34   FIG_35

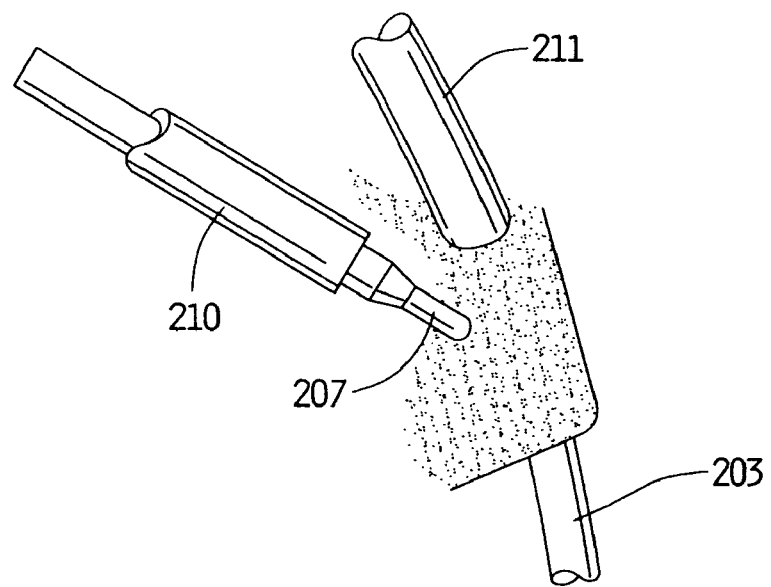
FIG_36
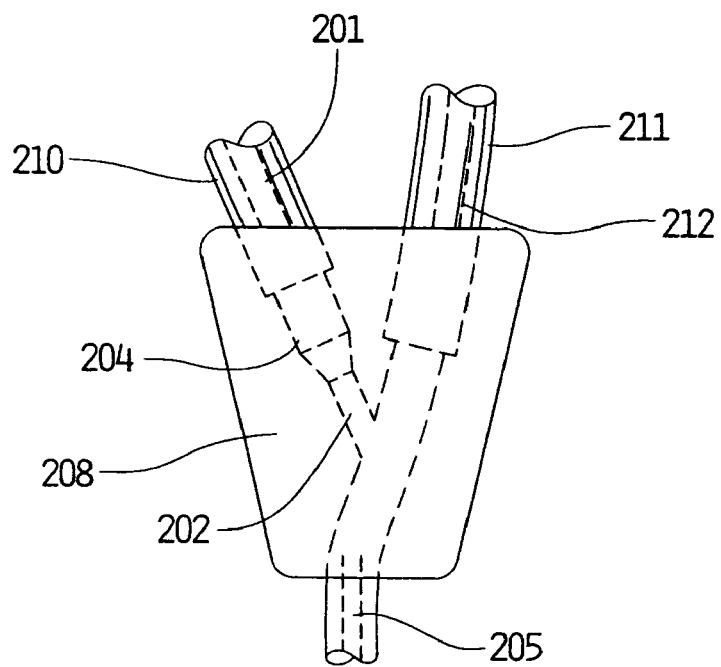
FIG_37

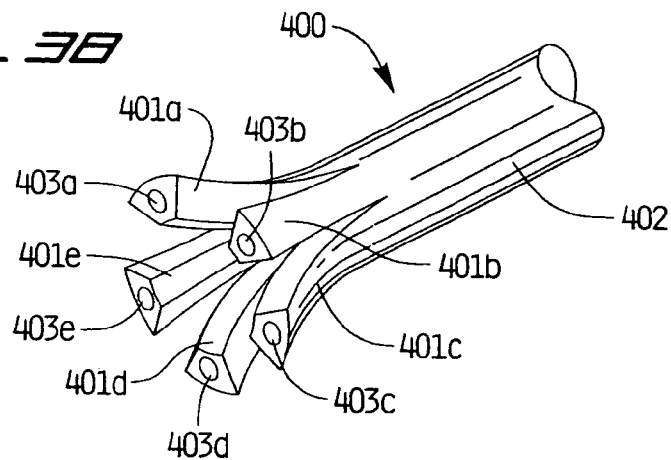
FIG_38
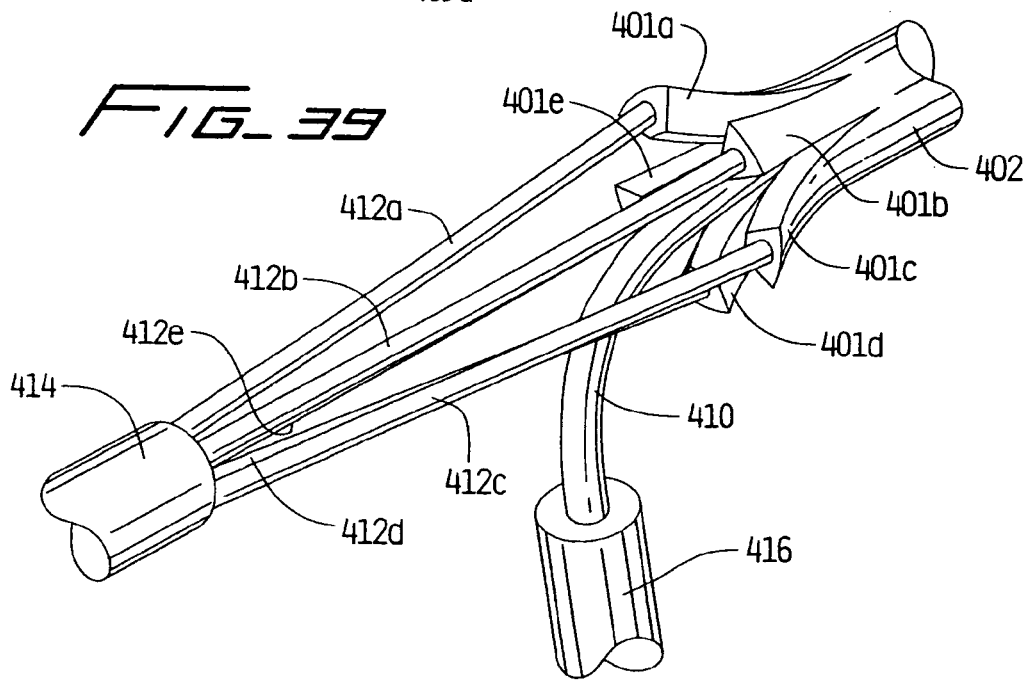
FIG_39
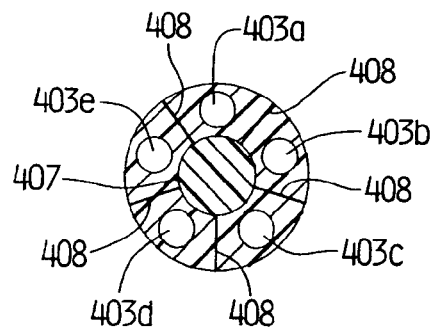
FIG_40

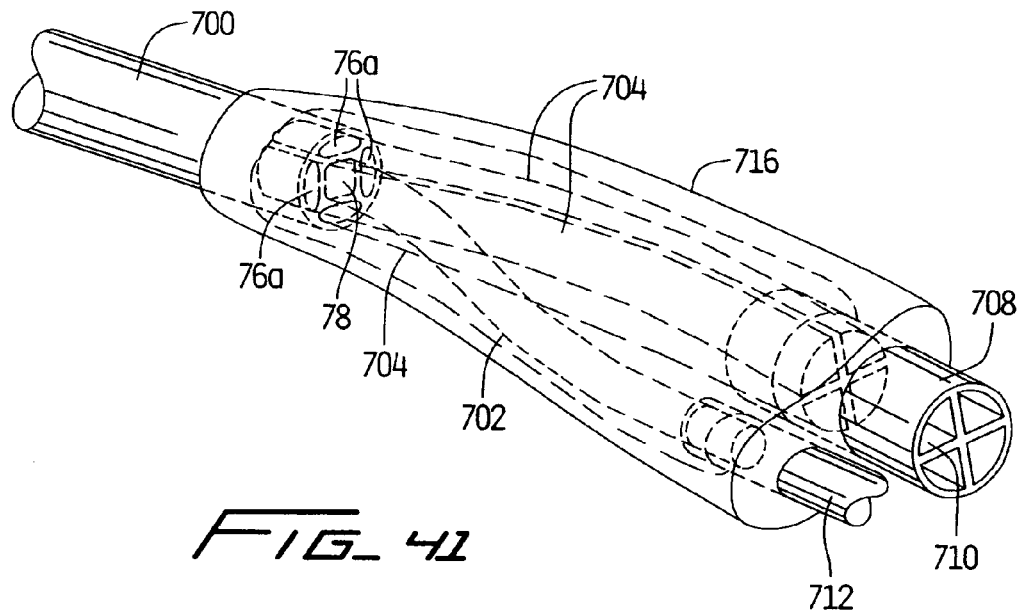
FIG_41
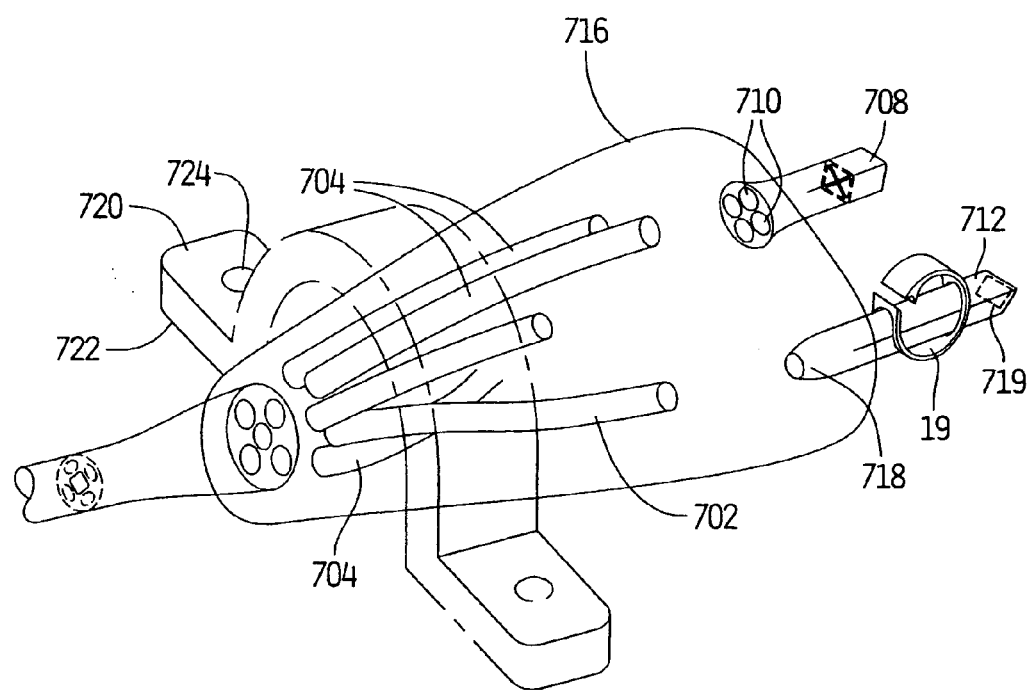
FIG_42

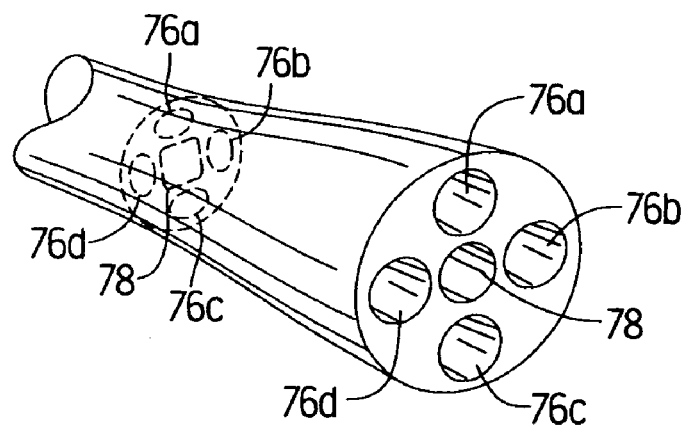
FIG_43
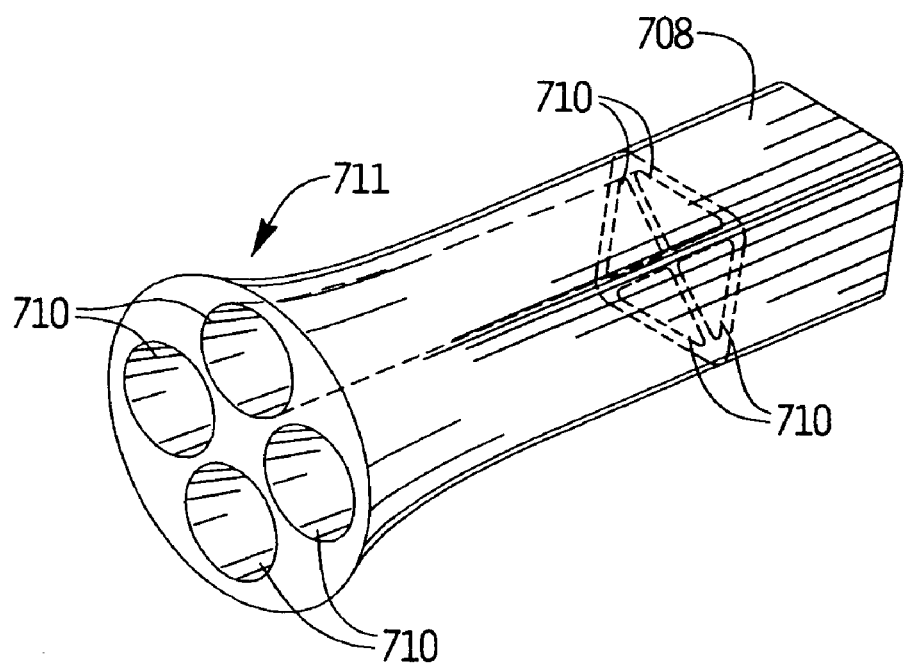
FIG_44

DIALYSIS CATHETER AND METHODS OF INSERTION

BACKGROUND

This application is a continuation of application Ser. No. 10/025,505, filed Dec. 19, 2001 now U.S. Pat. No. 6,858,019 which claims priority from provisional patent application Ser. No 60/260,592, filed Jan. 9, 2001, the entire contents of which is incorporated herein by reference.

TECHNICAL FIELD

This application relates to a catheter and more particularly to a multi-lumen dialysis catheter and over the wire methods of insertion of the dialysis catheter.

BACKGROUND OF RELATED ART

Hemodialysis is a well known method of providing renal (kidney) function by circulating blood. The kidneys are organs which function to extract water and urea, mineral salts, toxins, and other waste products from the blood with filtering units called nephrons. From the nephrons the collected waste is sent to the bladder for excretion. For patients having one or both defective kidneys, the hemodialysis procedure is life saving because it provides a machine to simulate the function of the kidneys.

In the hemodialysis procedure, blood is withdrawn from the patient's body through a catheter or tube and transported to a dialysis machine, also commonly referred to as a kidney machine. The catheter is typically inserted through the jugular vein and maneuvered into position through the superior vena cava into the right atrium to provide high blood flow. In the dialysis machine, toxins and other waste products diffuse through a semi-permeable membrane into a dialysis fluid closely matching the chemical composition of the blood. The filtered blood, i.e. with the waste products removed, is then returned to the patient's body. In some instances, the catheter may be left in place for several years. As can be appreciated, proper access to the patient's blood and transport of the blood to and from the dialysis machine for this extended period of time is critical to hemodialysis.

One example of a dialysis catheter currently being marketed is the MedComp Ash Split catheter. This catheter has two lumens, one for arterial flow and the other for venous flow, which are each D-shaped in cross-sectional configuration. The catheter is bifurcated at its distal end to separate the lumens and the catheter is manually split to the desired length for selected separation before insertion into the target area. Another well-known catheter is a Med Comp catheter which has the venous flow lumen terminating proximally, i.e. axially recessed, from the arterial flow lumen. Each of these lumens is also D-shaped in cross-sectional configuration.

These Medcomp dialysis catheters require numerous steps for insertion. The multiple insertion steps can be summarized as follows:

1. an introducer needle is inserted through a first incision site (first opening) to properly locate (access) the vessel, e.g. the right internal jugular vein;
2. a guide wire is inserted through the needle into the internal jugular vein and down through the superior vena cava into the inferior vena cava;
3. the introducer needle is withdrawn leaving the guidewire in place;
4. a tear away (peel away) sheath and dilator are inserted over the guidewire and through the first incision site to provide an access port for the dialysis catheter into the jugular vein, superior vena cava and right atrium;
5. a second incision is made in the chest wall to create a second opening;
6. a trocar is attached to the distal end of the dialysis catheter;
7. the trocar and dialysis catheter are pushed through the second incision and advanced to bluntly dissect the subcutaneous tissue to exit the first incision (opening) which was created by the introducer needle, thereby creating a subcutaneous tissue tunnel between the first and second openings;
8. the trocar is detached from the dialysis catheter leaving the catheter in place extending from the second opening, through the tissue tunnel and out the first opening;
9. the dilator and guidewire are removed, leaving the tear away sheath in place in the first incision which has been expanded by the dilator;
10. the dialysis catheter, which is protruding from the first incision, is inserted through the tear away sheath and advanced so its distal portion is positioned in the right atrium;
11. the sheath is separated, i.e. split, by pulling the tabs apart, and then pulled upwardly away from the dialysis catheter and removed from the body, leaving the catheter in place; and
12. the second incision is closed and the dialysis catheter, which is connected through tubes to the dialysis machine, is left in place an extended period of time to provide blood circulation to and from the dialysis machine.

(Alternatively, in the foregoing method, the trocar can be forced through a third incision exiting adjacent the first incision, and then inserted through the introducer sheath positioned in the first incision.)

This multiple step process of inserting the Medcomp dialysis catheter is time consuming and complicates the surgical procedure. These multiple steps add to the cost of the procedure, not only because of the additional surgeon's time but because additional components, such as the tear-away sheath, are required which increases the overall cost of the catheter system. Also, removal of the dilator increases the tendency of the sheath to kink causing difficulties in catheter insertion.

The use of the tear away sheath is also potentially problematic. The tear-away style sheath has lines of weakness to separate the sheath as it is pulled apart by the pull tabs to enable removal of the sheath. However, the sheath can potentially cause damage to the vessel wall as it is being pulled apart and can cause infection. Moreover, pulling the sheath laterally can enlarge the incision, thereby increasing the difficulty of closing the incision at the end of the procedure. Also, since the sheath is pulled in the proximal direction for removal, it could pull the catheter proximally as well, thereby pulling it away from the desired site, and requiring repositioning. The edges of the tear away can also lacerate the surgeon's glove and finger.

An additional potential risk with utilizing tear away sheaths is that air embolism can occur. During the time the surgeon withdraws the dilator from the sheath and inserts the catheter, a passageway through the sheath to the vessel is open. If the patient inhales during this catheter exchange, an air bubble can enter the vascular system and obstruct the vessel, potentially causing stroke or even death.

It would therefore be advantageous if a dialysis catheter insertion method could be provided which reduces some of the foregoing procedural steps, thereby decreasing the complexity of the procedure and decreasing the hospital and surgeon costs. It would also be advantageous if such dialysis catheter insertion method could be provided which would be less traumatic and avoid the foregoing problems associated with the use of a tear-away sheath, such as increased risk of air embolism, trauma to the vessel wall, incision enlargement and dislodgement of the catheter.

Another area of dialysis catheter insertion, which needs improvement, is guiding the catheter to the target site. Dialysis catheters are composed of flexible tubing to minimize damage to the vessel wall during insertion and use. This flexibility, however, oftentimes results in kinking of the catheter since the catheter must navigate curves to reach the target vessel. This kinking can adversely affect blood flow. Also, the catheter needs to have some degree of stiffness to enable directing the catheter around the curves of the vessels. The stiffness, however provides its own risks since if the catheter is not properly directed, the catheter can inadvertently be forced against the vessel wall, thereby puncturing or damaging the vessel. Several different approaches have been discussed in the prior art to increase stiffness of catheters such as providing a distal tip of stiffer material to guide the catheter as in U.S. Pat. No. 5,957,893, using materials of different durometers in various portions of the catheter (U.S. Pat. No. 5,348,536), placing an additional concentration of material in the tip as in U.S. Pat. No. 4,583,968, or providing reinforcing strips, obturators or tubes within the catheter body to increase the rigidity (e.g. U.S. Pat. Nos. 4,619,643, 4,950,259 5,221,255, 5,221,256, and 5,246,430). The need however exists to improve the balance between flexibility and stiffness. Thus it would be advantageous to provide a catheter with sufficient flexibility to accommodate anatomical curves of the patient while still having sufficient stiffness to enable guiding the flexible catheter tubing atraumatically through the length of the vessels.

In navigating vessels to access the target site, such as the right atrium, it is desirable to provide the smallest catheter profile, i.e. the smallest outer diameter catheter body. This profile facilitates insertion through smaller vessels as it reduces the likelihood of the catheter engaging the wall of the vessel and reduces trauma to the vessel by minimizing frictional contact with the vessel wall. However, the desire for smaller diameter catheters must be balanced against the need for providing sufficient sized lumens to enable proper blood flow. If the lumens are too small, sufficient blood flow may not be able to be maintained and the blood can be damaged during transport. Also, a sufficient relationship must be maintained between the size of the lumens and the overall diameter of the catheter to maintain the structural integrity of the catheter.

Numerous attempts have been made in the prior art to optimize the multi-lumen configuration. In some approaches, such as disclosed in U.S. Pat. Nos. 4,568,329 and 5,053,023, inflow and outflow lumen are provided side by side in D-shaped form. In other approaches, such as those disclosed in U.S. Pat. Nos. 4,493,696, 5,167,623 and 5,380,276 the inflow and outflow tubes are placed in concentric relation. Other examples of different lumen configurations are disclosed in U.S. Pat. Nos. 5,221,256, 5,364,344, and 5,451,206. The lumen configuration must accommodate two competing factors: keeping the catheter as small as possible to facilitate insertion while keeping the lumens as large as possible for blood flow. This balance must be achieved while maintaining the structural integrity of the catheter. It would therefore be advantageous to provide a catheter which reaches an optimum compromise between these two competing factors.

Another important feature of dialysis catheters is the suction openings to withdraw blood. Keeping the suction openings clear of thrombolytic material and away from the vessel wall is clearly essential to dialysis function since an adequate supply of blood must be removed from the patient to be dialyzed. However, a problem with prior dialysis catheters is that during blood withdrawal, as suction is being applied through the catheter openings and lumen, the suction can cause the catheter to be forced against the side wall of the vessel, known as "side port occlusion", which can block the opening and adversely affect the function of the catheter by enabling only intermittent suction. In fact, the opening can become completely blocked, thereby preventing necessary intake of blood, i.e. venous flow. Fibrin sheath growth around the outside of the catheter can occur since dialysis catheters are oftentimes implanted for several months or even years. This fibrin growth, caused by the body's attempt to reject the catheter as a foreign body, could result in blocking of the suction holes.

The need therefore exists for an improved dialysis catheter which facilitates the surgical dialysis procedure. Such catheter would advantageously reduce the catheter insertion time, simplify the catheter insertion process, eliminate the need for a peel-away introducer sheath, decrease the chances of infection, reduce unwanted kinking of the catheter during insertion, strike an optimal balance between overall catheter and lumen size, and improve the suction capability to avoid hampering of venous flow.

SUMMARY

The present invention overcomes the disadvantages and deficiencies of the prior art. The present invention provides a method of inserting a dialysis catheter into a patient comprising:

inserting a guidewire into the jugular vein of the patient through the superior vena cava, and into the inferior vena cava;

providing a trocar having a lumen and a dissecting tip;

inserting the trocar to enter an incision in the patient to create a subcutaneous tissue tunnel;

threading the guidewire through the lumen of the trocar so the guidewire extends through the incision;

providing a dialysis catheter having first and second lumens;

removing the trocar; and inserting the dialysis catheter over the guidewire through the incision and through the jugular vein and superior vena cava into the right atrium.

The method preferably comprises the step of inserting a dilator prior to the step of inserting the dialysis catheter. The method preferably further comprises the step of temporarily inserting a stiffening member in the first lumen of the catheter to facilitate insertion of the catheter. The method of inserting the stiffening member and advancing the catheter preferably includes the steps of twisting the stiffening member and securing the stiffening member to a proximal portion of the catheter to stretch the catheter to reduce a least a portion of the outside diameter of the catheter.

Preferably, the method also comprises the steps of removing the guidewire and leaving the catheter in position for at least several days to enable blood inflow through the first lumen and blood outflow through the second lumen to dialyze the patient's blood. The step of leaving the catheter in place to enable blood outflow and inflow preferably further comprises the step of enabling blood outflow through at least one opening in a wall of the catheter and enabling blood inflow through at least one opening in a distal portion of the catheter.

Also provided is a method of inserting a dialysis catheter into a patient comprising:

inserting a guidewire into the vein of a patient;

advancing a trocar through an incision in the patient to create a subcutaneous tissue tunnel;

retracting the guidewire through the subcutaneous tissue tunnel and incision utilizing the trocar;

removing the trocar;

inserting a dialysis catheter over the guidewire through the incision and subcutaneous tissue tunnel and through the vein of the patient; and securing the dialysis catheter to the patient.

The step of retracting the guidewire may comprise the step of inserting the guidewire through an opening in the trocar. The opening may extend longitudinally through the trocar and the step of inserting the guidewire may comprise the step of threading the trocar over the guidewire such that the guidewire exits from a proximal portion of the trocar.

The present invention also provides a method of inserting a dialysis catheter into a right atrium of a patient is also provided comprising:

providing a dialysis catheter having a lumen;

inserting a guidewire into the inferior vena cava of the patient;

inserting a stiffening member through the lumen in the catheter;

inserting a guidewire through the stiffening member and advancing the dialysis catheter and stiffening member over the guidewire into the vein and into the right atrium of the patient; and removing the guidewire leaving the dialysis catheter in place for a period of time.

The step of inserting the stiffening member preferably comprises the step of inserting the stiffening member such that a dilating distal tip of the stiffening member extends distally of the catheter.

The method preferably further comprises inserting a tunneling member through an incision to create a tissue tunnel and to retrieve the guidewire. Preferably the guidewire is inserted through a longitudinally extending opening formed in the tunneling member. The dialysis catheter is preferably inserted subcutaneously over the guidewire through a tissue tunnel prior to the step of advancing the dialysis catheter into the vein.

The step of advancing the dialysis catheter over the guidewire may include the step of forming a loop in the catheter corresponding to a loop formed in the guidewire prior to fully advancing the catheter into the right atrium.

The present invention also provides a dialysis catheter comprising a catheter body having a proximal portion, a distal portion, a first longitudinally extending central lumen configured to deliver blood, and at least three longitudinally extending lumens positioned radially of the central lumen and configured to withdraw blood from a patient. At least one blood delivery opening is formed in the distal portion of the catheter body and in fluid communication with the first lumen and configured for passage of blood therethrough. At least three blood withdrawal openings are formed in the outer wall of the catheter body, wherein each of the openings is in fluid communication with one of the at least three lumens and is configured for passage of blood from a patient.

A stiffening member may be provided which is positionable within the catheter in abutment with a shoulder or threadedly attached in an alternate embodiment. The stiffening member places the catheter body in tension, and torquing the stiffening member stretches the catheter body to reduce at least a portion of an outer diameter of the catheter body. The stiffening member preferably includes a longitudinally extending lumen for receiving a guidewire. A stiffening insert having a first stiffness greater than a second stiffness of the distal tip portion of the catheter can also be provided having a lumen formed therein communicating with the first lumen.

The distal tip portion of the catheter has a bullet nose configuration in one embodiment and tapers to a reduced diameter region in another embodiment. In one embodiment, at least two side ports are formed in an outer wall of the distal tip portion and are in fluid communication with the first lumen of the distal tip portion and positioned proximally of the stiffening insert.

The present invention also provides a system for placement of a dialysis catheter comprising a tunneling trocar and a dialysis catheter. The system comprises a trocar having an elongated tubular portion and a lumen extending longitudinally through the tubular portion. The tubular portion terminates in a dilating tip configured to dilate tissue and create a subcutaneous tissue tunnel. The lumen has a first internal diameter configured to removably receive a guidewire therethrough for retrieval of the guidewire. The dialysis catheter has a first lumen configured for blood delivery and a second independent lumen configured for blood withdrawal from the patient. At least a portion of the catheter has an outer diameter configured for insertion through the subcutaneous tissue tunnel and one of the lumens is configured to receive the guidewire for over the wire insertion of the dialysis catheter through the tissue tunnel when the trocar is removed.

BRIEF DESCRIPTION OF THE DRAWINGS

Preferred embodiment(s) of the present disclosure are described herein with reference to the drawings wherein:

FIG. 1 is a plan view of a first embodiment of the multi-lumen catheter of the present invention being inserted through the right internal jugular vein and superior vena cava into the right atrium of a patient's body;

FIG. 2 is a plan view illustrating the multi-lumen catheter of FIG. 1 being inserted through the left internal jugular vein and superior vena cava into the right atrium;

FIG. 3 is an isometric view of the first embodiment of the multi-lumen catheter of the present invention and showing the direction of insertion of the stiffening rod;

FIG. 4A is a side view of a first embodiment of a stiffening rod of the present invention insertable through the catheter of FIG. 3 to facilitate catheter insertion;

FIG. 4B is a side view of an alternate embodiment of the stiffening rod of the present invention having a series of mounting threads at its distal end;

FIG. 5 is perspective view of the distal portion of the multi-lumen catheter of FIG. 3 and showing a guidewire extending through the central lumen;

FIG. 6A is a longitudinal cross-sectional view taken along lines 6A-6A of FIG. 5;

FIG. 6B is a longitudinal cross-sectional view similar to FIG. 6A except showing an alternate embodiment of the catheter having internal threads for securing the stiffening rod of FIG. 4B;

FIG. 7 is a transverse cross sectional view taken along lines 7-7 of FIG. 6A;

FIG. 8 is a transverse cross sectional view taken along lines 8-8 of FIG. 6A:

FIG. 9A is a transverse cross-sectional view similar to FIG. 8 except showing a second alternate embodiment of the lumen configuration of the catheter of the present invention;

FIG. 9B is a transverse cross-sectional view similar to FIG. 8 except showing a third embodiment of the lumen configuration of the catheter of the present invention;

FIG. 9C is a transverse cross-sectional view similar to FIG. 8 except showing a fourth embodiment of the lumen configuration of the catheter of the present invention;

FIG. 10 is a transverse cross-sectional view similar to FIG. 8 except showing a fifth embodiment of the lumen configuration of the catheter of the present invention;

FIGS. 13-15 illustrate an alternate embodiment of the distal tip of the catheter of the present invention and the method steps for forming the tip wherein:

FIGS. 13A and 13B are perspective and cross-sectional views, respectively, of the tip before formation shown receiving a stiffening insert;

FIGS. 14A and 14B are perspective and cross-sectional views, respectively, of the tip once the stiffening inserted has been placed therein;

FIGS. 15A and 15B are perspective and cross-sectional views, respectively, of the distal tip formed into a bullet nose configuration and showing side holes formed therein;

FIG. 16A is a perspective view of a distal portion of another alternate embodiment of the multi-lumen catheter of the present invention having a series of spacer wires and showing a guidewire extending therethrough;

FIG. 16B is a longitudinal cross-sectional view of the distal portion catheter of FIG. 16A showing the spacer wires in the extended position;

FIG. 16C is a longitudinal cross-sectional view similar to FIG. 16A except showing the profile of the spacing wires and catheter body reduced as the stiffening rod of FIG. 4A is inserted into the central lumen over the guidewire to stretch the catheter during insertion;

FIG. 17A is a perspective view of a distal portion of yet another alternate embodiment of the catheter of the present invention having a series of integral spacer ribs;

FIG. 17B is a longitudinal cross-sectional view of the distal portion of catheter of FIG. 17 showing the spacer ribs in the extended position;

FIG. 17C is a longitudinal cross-sectional view similar to FIG. 17A except showing the profile of the spacer ribs and catheter body reduced as the stiffening rod of FIG. 4A is inserted into the central lumen to stretch the catheter during insertion;

FIG. 18 is a perspective view of a distal portion of another alternate embodiment of the multi-lumen catheter of the present invention having a tapered tip;

FIG. 19 is a longitudinal cross-sectional view of the distal portion of the catheter of FIG. 18 showing the stiffening rod positioned through the central lumen of the catheter over the guidewire;

FIG. 20 is a perspective view of a distal portion of yet another alternate embodiment of multi-lumen catheter of the present invention;

FIG. 21 is a perspective view of a first embodiment of a trocar of the present invention having a barbed proximal end for attachment to the catheter for creating a subcutaneous tissue tunnel and for pulling the catheter through the tissue tunnel;

FIG. 22 illustrates an alternate embodiment of the trocar of the present invention having a lumen for receiving a guidewire;

FIG. 23 illustrates the trocar of FIG. 22 being withdrawn after a subcutaneous tissue tunnel has been created;

FIG. 24A is a bottom view of another alternate embodiment of the trocar of the present invention having a lumen for receiving a guidewire;

FIG. 24B is a longitudinal cross-sectional view of the distal end portion of the trocar of FIG. 24A;

FIGS. 25-28 illustrate the surgical method steps for inserting the multi-lumen catheter of FIG. 3 through the right internal jugular vein and superior vena cava into the right atrium wherein:

FIG. 25 shows the introducer needle being inserted through the right jugular vein and the guidewire being inserted through the right jugular vein, through the superior vena cava and into the right atrium;

FIG. 26 illustrates the needle introducer removed leaving the guidewire in place in the right internal jugular vein, superior vena cava and right atrium;

FIG. 27 illustrates the trocar of FIG. 22 being inserted through a first incision site and exiting a second incision site to create a subcutaneous tissue tunnel adjacent the incision site for the introducer needle;

FIG. 28C illustrates the multi-lumen catheter of FIG. 3 inserted over the guidewire through the tissue tunnel, and curved down into the right internal jugular vein, superior vena cava and right atrium;

FIGS. 29A-29G illustrate the steps for an alternate method of inserting the multi-lumen catheter of FIG. 3 through the right internal jugular vein and superior vena cava into the right atrium wherein the trocar creates a tissue tunnel with an exit opening at the incision cite where the needle and guidewire are introduced, wherein:

FIG. 29A illustrates the trocar of FIG. 22 inserted over the guidewire through a first incision site, creating a subcutaneous tissue tunnel, and exiting the incision site created for insertion of the introducer needle and guidewire;

FIG. 29B illustrates the trocar being removed, leaving the guidewire in place extending through the tissue tunnel and forming a loop adjacent the needle incision site; and FIG. 29C illustrates the multi-lumen catheter of FIG. 3 being inserted over the guidewire for passage through the tissue tunnel;

FIG. 29D illustrates the catheter inserted through the subcutaneous tissue tunnel and forming a loop corresponding to the loop formed in the guidewire, FIG. 29E illustrates the catheter extending through the subcutaneous tissue tunnel and being inserted further along the guidewire down into the right internal jugular vein;

FIG. 29F is a view similar to FIG. 29E except showing the guidewire being removed; and FIG. 29G illustrates the catheter in place extending through the subcutaneous tissue tunnel and advanced into the right internal jugular vein, superior vena cava and right atrium;

FIG. 30 illustrates an alternate method of retracting the guidewire through the subcutaneous tissue tunnel formed by the trocar;

FIGS. 31-37 illustrate a method for manufacturing a first embodiment of the hub of the multi-lumen catheter of FIG. 3 wherein:

FIG. 31 illustrates a slit formed in the outer wall of the catheter;

FIG. 32 is a view similar to FIG. 31 except showing in phantom the central arterial lumen of the catheter;

FIG. 33 is a transverse cross-sectional view taken along lines 33-33 of FIG. 32;

FIG. 34 illustrates a pin inserted through the slit in the outer wall of the catheter;

FIG. 35 illustrates the tubing inserted over the pin;

FIG. 36 illustrates the injection of soft material over the pin and catheter tube to form the catheter hub which retains the lumen connector tubes in position;

FIG. 37 illustrates the hub resulting from the injection molding process enabling one connector to communicate with the inflow (arterial) lumen and the other connector to communicate with the multiple outflow (venous) lumens;

FIGS. 38-40 illustrate an alternate embodiment of the hub of the multi-lumen catheter of FIG. 3 wherein;

FIG. 38 illustrates a perspective view of the proximal end of the catheter body split into five segments to accommodate the separate connector tubes;

FIG. 39 is a perspective view illustrating the connector tubes inserted into the respective lumens of the catheter body; and FIG. 40 is a transverse cross-sectional view illustrating the cuts made in the catheter wall to form the separate segments.

FIG. 41 is a perspective view of another alternate embodiment of the hub of the catheter of the present invention having the lumen configuration of FIG. 9C;

FIG. 42 is an exploded view of the hub and tube structure of FIG. 41;

FIG. 43 is an enlarged perspective view showing the transition of the venous holes from a substantially oval to a substantially round configuration at the flared proximal portion of the catheter; and FIG. 44 is an enlarged perspective view showing the multi-lumen extension tube tapering proximally and transitioning from substantially circular venous holes to substantially triangular holes.

DETAILED DESCRIPTION OF PREFERRED EMBODIMENTS

Figure 11:
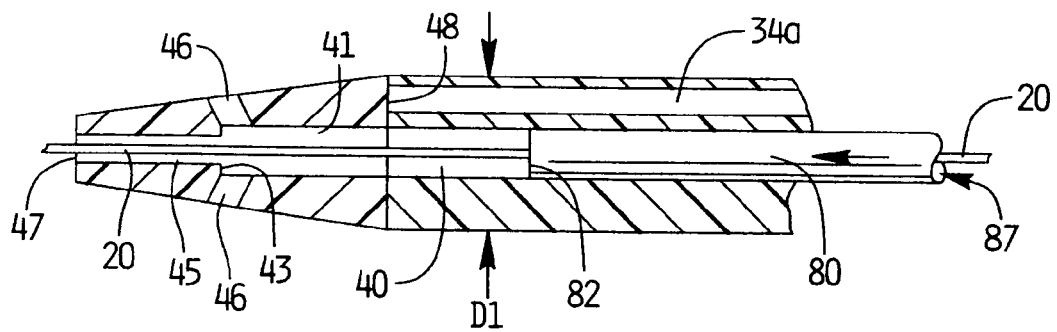
FIG. 11 is a longitudinal cross sectional view of the distal end portion of the catheter of FIG. 3 illustrating the stiffening rod of FIG. 4A being inserted through the central lumen of the catheter.

Referring now in detail to the drawings where like reference numerals identify similar or like components throughout the several views, the first embodiment of the catheter of the present invention is designated generally by reference numeral 10. The catheter 10 is typically inserted into an area of high velocity blood flow to ensure sufficient blood can be transported from the body for dialysis. FIG. 1 illustrates the catheter 10 inserted through the right internal jugular vein "a", into the superior vena cava "b", inferior vena cava "d" and into the right atrium "c"; FIG. 2 illustrates the catheter 10 inserted into the left internal jugular vein "d", into the superior vena cava "b" and into the right atrium "c". Insertion into the right atrium, from either the right or left side provides the necessary high blood flow to the dialysis machine. Note that the catheter body (catheter tube) 11 is sufficiently flexible to enable it to bend to accommodate the anatomical curves as shown.

Catheter 10 has a catheter body or catheter tube 11 having a distal end portion 31, a proximal end portion 33, and an intermediate portion 35. Distal portion 31 terminates in nose 32 which is illustratively substantially conical in shape. Proximal end portion 33 includes hub 12, where the lumens formed within catheter tube 11 are connected, i.e., transition, to the respective inflow and outflow tubes, 16, 18, respectively, having respective proximal threads 15, 9 to enable return and withdrawal of blood for dialysis. Conventional tube clamps 17 and 19 cut off blood flow through inflow and outflow tubes 16, 18 as desired. As used herein, the terms "inflow" and "outflow" refer to the direction of blood flow with respect to the patient's body such that "inflow" refers to flow from the dialysis machine and delivered to the body while "outflow" refers to flow withdrawn from the body and transported to the dialysis machine.

As shown, intermediate portion of catheter 10 extends through subcutaneous tissue tunnel "t", and curves downwardly toward the target site, e.g. the right atrium. This tunnel "t" secures the catheter in place for dialysis for a period of weeks, or even months, with fibrous cuff 36 (FIG. 3) enabling tissue ingrowth. The formation of the tunnel "t" and the insertion of the catheter 10 therethrough will be discussed below in conjunction with the discussion of the catheter insertion method.

It should be appreciated that although the catheter is shown emerging from the tissue tunnel "t" at a second incision site, preferably, the tissue tunnel would not have an exit opening at a second site but instead would exit through the same incision through which initial access is made by the needle and dilator into the internal jugular vein "a". This is described in more detail below.

A series of lumens are formed in catheter tube 11 for transporting blood to and from a dialysis machine. As is well known in the art, a dialysis machine essentially functions as a kidney for patients suffering from kidney failure. Blood is removed from the patient and transported to the dialysis machine where toxins are removed by diffusion through a semi-permeable membrane into a dialysis fluid. The filtered blood is then returned through the catheter body to the patient.

More specifically, and with reference to FIGS. 5, 6A, 7 and 8, details of the catheter lumens will now be described. Central longitudinal lumen 40 is formed within catheter tube 11, extends the entire length and is designed to transport filtered blood to the patient. Lumen 40 is also configured to receive a guidewire 20 to direct the catheter to the desired position. Lumen 40 extends to nose 42, and terminates in region 37 where it aligns with central longitudinal lumen 41 of nose 42. Central lumen 41 of nose 42 communicates with narrowed lumen 45, terminating in distal opening 47 to communicate with the patient's body so blood can be delivered through distal opening 47. Lumens 41 and 45 also receive guidewire 20. Thus, lumen 40, lumen 41 and narrowed lumen 45 together form a central lumen enabling blood to be delivered from the dialysis machine to the patient. The transition from lumen 41 into narrowed lumen 45, forms a stop or shoulder 43, the function of which will be described below.

Nose 42 also includes side arterial (delivery) openings 46 formed through the outer wall 44 wall in fluid communication with lumen 41, also functioning to return blood to the patient's body. Side openings or ports 46 are preferably angled outwardly as shown to facilitate delivery of blood in the direction of blood flow and lessen mechanical hemolysis. These additional openings help maintain the desired flow volume by distributing the blood through multiple holes. Although only four openings are shown, it is contemplated that additional or fewer openings can be provided and the openings can be axially displaced with respect to each other. Additional set(s) of openings can also be provided spaced proximally or distally from side openings 46.

In this embodiment, nose $42$ forms the distal tip portion and is composed of a different material than the other portions of the catheter body 11 and is welded or attached by other means to the catheter body 11. The tip (nose) in this embodiment is composed of a stiffer material to facilitate tunneling and blunt dissection through tissue. The nose could alternatively be composed of a softer material, thereby being less traumatic upon contact with the vessel wall. However, in a preferred embodiment, the nose is composed of the same material as the catheter body, having a small stiffener member embedded therein. This configuration is described in detail below in conjunction with FIGS. 13-15.

Catheter 10 also has a series of venous (withdrawal) lumens 34a-34e, extending longitudinally along the length of the catheter body 11, each terminating at surface 48 of nose 42. In the preferred embodiment, shown in the cross-sectional view of FIG. 8, the lumens 34 are oval-like in configuration, with opposite curved walls 37a, 37b and opposite substantially flat walls 39a, 39b. These spaced apart lumens have solid material between them therefore increasing the structural integrity of the catheter body 11. The lumens 34a-e are independent from one another through the distal, intermediate and proximal portions 33, 35, 31 of the catheter body 11, until the hub 12 where the lumens 34a-34e connect to a common connector tube. This is described in more detail below. Lumens 34a-34e, as shown, are symmetrically positioned and radially displaced from the central arterial lumen 40.

With continued reference to FIGS. 5 and 6A, a series of side openings or ports 50 are provided in the outer wall 14 of catheter body 10. These openings 50a, 50b, 50c, 50d, and 50e are each in fluid communication with a respective outflow lumen 34a-34e and are designed and configured to withdraw blood from the patient's body for delivery to the dialysis machine. A second set of openings 52a-52e, spaced proximally from openings 50a-50e, is also in communication with a respective lumen 34a-34e. Only three of the side openings 50,52 are shown in FIG. 5, it being understood that the other three openings are positioned on the other side of the catheter, preferably symmetrically placed to accommodate the circumferential arrangement of the venous lumens 34a-34e.

Although lumens 34a-34e are isolated along a substantial length of the catheter, they preferably have a common flow source at the proximal portion 33 of the catheter 10. This is described in more detail below.

In the embodiment of FIG. 8, the arterial lumen size preferably ranges from about 0.006 inches to about 0.008 inches in cross-sectional area, and is more preferably 0.007 inches. The cross-sectional area of each of the venous lumens 34 preferably ranges from about 0.002 inches to about 0.004 inches, and more preferably about 0.003 inches, bringing the total cross-sectional area of the venous return lumens to about 0.01 inches to about 0.02 inches, and more preferably about 0.015. This means that the ratio of total cross sectional area of the arterial lumen to the venous lumen is about 1 to about 2.1. Other dimensions are also contemplated.

It should be appreciated that although five separate lumens 34 are shown, a fewer or greater number can be provided. Also, although two sets of side openings are shown (set 50 and set 52), a fewer or greater number of sets can be provided, and a fewer or greater number of openings in each set could be provided.

Alternative lumen configurations spaced circumferentially are illustrated in FIGS. 9A, 9B, 9C and 10. In FIG. 9B, three arc-shaped lumens 60a, 60b, 60c are positioned around the arterial central lumen 40'. These larger sized lumens provide for additional venous flow but result in the reduction of the strength of the catheter wall due to the less wall material as compared to the lumen configuration of FIG. 8. In FIG. 9A, five lumens 66a, 66b, 66c, 66d and 66e are provided. These lumens have more of a rectangular (or trapezoidal) shape with one pair of opposing walls having a straighter configuration than the lumen configuration of FIG. 8. As shown, the other pair of opposing walls has a slight curvature. In FIG. 9C, four oval-like venous lumens 76a, 76b, 76c and 76d are positioned around a substantially square central lumen 78. This lumen configuration provides for a substantially sized central lumen and sufficient room between the central lumen 78 and each of the venous lumens 76a-76d for the catheter walls for flex. In FIG. 10, five lumens 70a-70e of circular cross-section are provided around the central lumen 40", adding to the stability of the catheter by increasing the wall material, but reducing the overall venous lumen size as compared to the embodiment of FIG. 8. Preferably, the venous lumens in each of these embodiments are independent from one another along the substantial length of the catheter.

Fewer or greater number of lumens could be provided and lumens of other configurations are also contemplated. This positioning of the venous lumens in a circle-like array around the catheter, i.e. radially displaced from the center of the catheter, more evenly distributes the vacuum, as compared to a side by side venous/arterial lumen configuration, and ensures constant return flow since if one of the lumens becomes stuck against the vessel wall or otherwise clogged, the remaining lumens will maintain adequate flow. The openings in the sidewalls communicating with the lumens can also be elongated instead of circular, creating a series of longitudinally extending openings for entry of suctioned blood. This version of elongated openings is shown for example in FIGS. 18 and 20 described in detail below.

To facilitate insertion, the catheter is configured to receive an insert member or stiffening member in the form of a stiffening rod which stretches the catheter to reduce its profile to aid in over the wire insertion and better navigate through small vessels. That is, the stiffening rod is inserted into central lumen 40 of catheter 10 and torqued to stiffen the flexible catheter for ease in over the wire insertion and navigation through the small vessels, and to reduce the outer diameter of the catheter body by stretching it during insertion. After placement of the catheter 10, the stiffening rod is removed, allowing the catheter to return to its higher profile position with the lumens of the necessary size for blood transport to and from the body. Two embodiments of the stiffening rods are illustrated in FIGS. 4A and 4B and are shown prior to insertion into the catheter 10 in FIG. 3.

Turning to the first embodiment of the stiffening rod illustrated in FIG. 4A, the stiffening rod is designated generally by reference numeral 80. Stiffening rod 80 has a distal tip 82, a proximal end portion 85 and an internal lumen 87 extending therethrough (see FIG. 11). Stiffening rod 80 is inserted through the proximal end of inflow tube 16, in the direction of the arrow of FIG. 11, over the guidewire 20 (which extends through lumen 87 and through central lumen 40 until distal tip 82 abuts shoulder or stop 43 as shown in FIG. 12. The proximal end portion 85 of stiffening rod 80 has a threaded portion 81 which is screwed onto screw thread 15 of inflow tube 16. This temporarily secures the stiffening rod 80 within the catheter 10 during insertion. This threaded mounting requires the stiffening rod 80 to be manually twisted, thereby torquing rod 80 as it presses forwardly and applies a force against shoulder (abutment surface) 43 to stretch the catheter body 11 to reduce its outer diameter. It is contemplated in one embodiment, for example, that the catheter body 11 can be reduced in diameter from about 0.215 millimeters to about 0.207 millimeters by the stiffening rod 80. (Other size reductions are also contemplated). This reduction in catheter body diameter or profile is represented by the arrows D1 and D2 in FIGS. 11 and 12, respectively, which show the change in dimension effectuated by the stiffener rod 80.

Figure 12:
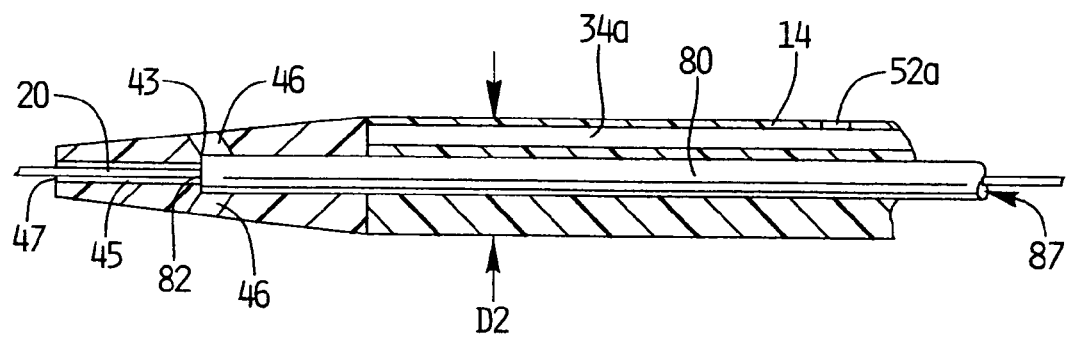
FIG. 12 is a longitudinal cross sectional view similar to FIG. 11 except showing the stiffening rod fully positioned within the central lumen, in abutment with the stop in the distal tip.

After the catheter 10 is positioned at the desired site, the stiffening rod 80 is unthreaded from the proximal thread 15 of inflow tube 16 and removed from the central lumen 40 of the catheter 10 and from the inflow tube 16, thereby allowing the catheter to return to its normal profile of FIG. 11.

It should be appreciated that stiffening rod 80 can alternatively be temporarily attached at its proximal end to the inflow tube 16 by other means such as a bayonet lock, snap fit, etc. The rod could first be manually twisted and then mounted by these various means for retention in its torqued position.

An alternate embodiment of the stiffening rod is illustrated in FIG. 4B and designated generally be reference numeral 90. Stiffening rod 90 has a proximal end portion 95 and a threaded distal end 92 which is threaded onto internal threads 251 of catheter 200 shown in FIG. 6B. A series of proximal threads 91 are screwed onto the threads 15 of the inflow tube 16 in the same manner as described above for stiffener rod 80. The stiffening rod 90 functions in the same manner as stiffening rod 80, i.e. to stretch the catheter during insertion to reduce its profile and to stiffen it to facilitate insertion, the only difference being the mechanical threaded attachment of the distal end of the stiffening rod 90 to the catheter 200 instead of abutting relation of stiffening rod 80 with shoulder 43 of catheter 10. Preferably, the distal threads 92 are first threaded onto internal thread 251, followed by attachment of the proximal threads 91 as the stiffening rod 90 is torqued. Stiffening rod 90, like stiffening rod 80, is preferably circular in cross-section, although other configurations are also contemplated.

Catheter 200 of FIG. 6B is identical to catheter 200 in all respects except for the threads 251 instead of shoulder 43 and lumen 241 which is uniform in diameter. Similar to catheter 10, catheter 200 has distal opening 247 and outflow side openings 246 in outer wall 244 communicating with lumen 241 in distal tip portion 242 at region 237, which communicates with central lumen 240. Venous inflow lumens 234a-234e terminate at wall 248 and have respective side openings 252a-252e and 250s-250e formed in the outer wall 214. Only one of the side openings 250a, 252a are shown in the longitudinal cross-sectional view of FIG. 6B.

As noted above, distal tip (nose) can be composed of a different stiffer material than the catheter body 11 or can be composed of a material having a higher durometer than the catheter body. This stiffer material will facilitate both tunneling through and dilating tissue. In an alternate preferred embodiment, however, the distal tip is composed of the same material as the catheter body but has a stiffening insert.

More specifically, the alternative nose (tip) configuration is illustrated in FIG. 15, with the method of manufacturing the tip shown in FIGS. 13 and 14. This nose or distal tip 104, is composed of the same material as the catheter body 108 and has a stiffening insert 110 inserted through central lumen 106 of nose 104. Central lumen 106 extends through the catheter body. The stiffening insert 110 is preferably composed of the same material as the catheter body 11 and nose 104, except it is made of a harder durometer material such as 72 shoreD vs. 85 shoreA for the catheter body 11. The material utilized can be, by way of example, urethane. For convenience, only the distal tip is shown, the remaining portions of the catheter 100 being identical to catheter 10.

The stiffening insert 110, preferably cylindrical as shown, has a hole 112 for receipt of the guidewire and for communication with central lumen 106. Insert 110 engages the inner wall surface 113 of central lumen 106. Lumen 106, proximal of side openings 114, will include either a stepped portion to provide an abutment surface (shoulder) for stiffening rod 80 or internal threads to mount rod 90 as described above.

The method of manufacturing this bullet shaped nose 104 will now be described in conjunction with FIGS. 13-15. Once cylindrical tube is formed, preferably by injection molding techniques, with central arterial lumen 106 and venous lumens 109a-109e, stiffening insert 110 is placed within central lumen 106 at the distalmost end and substantially flush with the distalmost edge 102 of the cylindrical tube.

Once the stiffening insert or slug 110 is placed within central lumen 106, the tube is formed into the bullet nose shape of FIGS. 15A and 15B, by a conventional radiofrequency or other heating process which allows the tip material to flow and form around the harder insert 110. After heating of the die and formation into this configuration, the material is cooled and thereby hardens to the configuration of FIG. 15 as the material fuses to the insert 110. A conventional core pin (not shown) can be used, inserted through the hole 112 and central lumen 106 during the forming process. When the material hardens, the pin is withdrawn to maintain these openings. After the forming process, side holes 114 are either cut or drilled through the wall 108 of catheter 100 to communicate with lumen 106 in the same manner as side holes 46 communicate with central lumen 40 of FIGS. 1-6.

FIGS. 16A-17C illustrate two alternate embodiments of the catheter of the present invention having spacers to minimize contact of the catheter body with the vessel wall. Provision of these spacers is optional. In the embodiment of FIGS. 16A-16C, catheter 150, similar to catheter 10, has a distal portion having a nose 154, a central arterial lumen 156 which also receives a guidewire 20, and a series (e.g. 5) of venous lumens 160-160. Arterial lumen 156 communicates with lumen 151 and narrowed lumen 153 of the nose 154, terminating in open distal end 158. A plurality of side openings 159 communicate with lumen 151 and function in the same manner as side openings 46 of catheter 10. Venous lumens 160 each terminate at side openings 161, similar to side openings 52 of venous lumens 34 of catheter 10. Although only one series of side openings 161 are shown, clearly additional arrays of side openings, positioned distally or proximally of side openings 161 could be provided. The venous lumen configuration can also vary in a similar manner as described above with respect to catheter 10. Thus, except for the spacers, catheter 150 is identical to catheter 10.

A plurality of spacer wires 164 are embedded in the wall 169 of the catheter 150 and are secured at region 158 by adhesive or other suitable means. In the normal configuration, spacer wires 164 bow slightly outwardly with respect to the outer wall 169 of the catheter 150 to reduce the likelihood of contact with the vessel wall. When the stiffening rod 80 is inserted over guidewire 20 and through central lumen 156, as shown in FIG. 16C, and edge 170 is forced against the abutment surface or stop 159, the catheter body is stretched and the spacer wires 164 stretch to a straightened position, substantially flush with the outer surface of wall 169. This reduces the profile of the catheter and ensures the spacer wires do not interfere with catheter insertion. When the stiffener rod 80 is withdrawn, the catheter returns to its normal position, and the spacer wires 164 bow outwardly as in FIGS. 16A and 16B. It should be appreciated that stiffening rod 90 can also be used with catheter 150 and would function to reduce the profile in the same manner as rod 80. Catheter 150 would then be provided with internal threads for mounting stiffening rod 90 as described above.

An alternative to spacer wires is illustrated in FIGS. 17A-17C. Catheter 180 is identical to catheter 150, except it is provided with integral ribs 194 proximal of nose 184. That is, similar to catheter 150, catheter 180 has a central arterial lumen 186 configured to receive guidewire 20 and stiffening rod 80 or 90. Lumen 186 communicates with lumen 181 and narrowed lumen 183 of the nose 184 which terminates in open distal end 188. Side openings 189 of nose 184 communicate with lumen 181. A series of independent venous lumens 190 are provided, terminating in side openings 192, similar to side openings 161 of catheter 150. Although only one series of side openings 192 are shown, clearly additional arrays, positioned proximally or distally of side openings 192 could be provided.

Spacer ribs 194 are formed by cutout portions in the wall 193 of the catheter 150. FIG. 17B illustrates the spacer ribs 194 in their normal position, outwardly bowed from the outer surface of the wall 193 of the catheter body. FIG. 17C illustrates the straightened or retracted position of the spacer ribs 194, where the ribs 194 are substantially flush with the outer surface of wall 193, after stiffener rod 80 of FIG. 4A (or rod 90 of FIG. 4B)) is inserted through central lumen 186 to stretch the catheter 150 for insertion in the manner described above.

FIGS. 18 and 19 illustrate another alternative embodiment of the catheter of the present invention. Catheter 500 has a distal tip 502 with a tapered region 510 transitioning to a reduced diameter region 504. The central lumen terminates in distal opening 506 for fluid delivery. Unlike the previously described embodiments, the distal opening 506 is the sole fluid delivery passageway into the body. However, it is also contemplated that additional side holes could be provided in the tip to provide additional arterial ports for blood delivery to the patient.

A series of venous openings 508 (only two are shown in the view of FIG. 18) are provided in the transition or tapered region 510 of the tip 502. These openings are elongated to provide additional area for suctioning. Each of the openings 508 communicates with a respective venous lumen 510 formed in the catheter. The venous lumen configuration (and arterial lumen configuration) can be in the form of those illustrated in FIGS. 7-10, or other variations, as described above.

Stiffening rod 520 is shown positioned in the central lumen of the catheter 500. Rod 520 is similar to the rods 80 and 90 described above except it extends distally of the distal tip 502 of catheter 500, has a tapered distal end 524 to facilitate tunneling and dilating tissue, and has a stepped portion to abut the internal structure of the catheter 500. More specifically, guidewire 20 is shown extending through the central lumen of stiffening rod 520. The stiffening rod 520 is inserted through the central lumen of catheter 500 and the stiffening rod 520 and catheter 500 are inserted over the guidewire 20, with the tapered tip 524 facilitating passage of the catheter as it dilates tissue.

Catheter 500 has a cylindrical insert 514 positioned in the distal tip, similar to insert 110 of FIG. 13A. The insert 514 is composed of a stiffer material to stiffen the tip of the catheter 500 to facilitate insertion. Insert 510 has an opening to receive stiffening rod 520 as shown. Shoulder 526 formed by the stepped portion abuts the insert 514, thereby functioning as a stop in a similar manner that shoulder 43 acts as a stop for stiffening rod 80 shown in FIG. 11, the difference being the shoulder is formed in the internal wall of the catheter rather than on the stiffening rod. Stiffening rod 520 thus acts in the manner as the aforedescribed rods 80, 90, i.e. pressing against the catheter tip portion to stretch the catheter for insertion, in addition to providing a tissue tunneling and dilation function.

FIG. 20 illustrates an alternative tip design of the catheter of the present invention. Catheter tip 602 has a bullet nose configuration, somewhat similar to the nose of FIG. 15, except having more of a progressive taper. Catheter tip 602 also has a series of elongated venous holes 608 (only two are shown in the view of FIG. 20). In all other respects, e.g. stiffening insert, stiffening rod, distal blood delivery opening 606, etc, catheter 600 is identical to catheter 500 of FIG. 18.

The method of insertion of the catheter of the present invention provides an entire over the wire system. This is achieved by the provision of trocar 300 illustrated in FIGS. 22 and 23. Trocar 300 has a lumen 304 formed therethrough (shown in phantom in FIG. 22) dimensioned for reception of guidewire 20. The lumen 304 extends the entire length of trocar 300, from a proximal opening 306 in handle 308 to a distal opening 310 (shown in phantom in FIG. 22) on the underside of the trocar 300 as viewed in FIG. 22. Distal opening 310 is adjacent the distal tip 302, at the region where it bends slightly upwardly. Note the lumen 304 of trocar 300 can be smaller than the outer diameter of the dialysis catheter, e.g. catheter 10, since it only needs to have an internal diameter of about 0.045 inches to receive the guidewire. The diameter of the catheter is typically 0.215 inches. The blunt distal tip 302 of trocar 300 bluntly dissects tissue to create a subcutaneous tissue tunnel for subsequent securement of the catheter.

FIGS. 24A and 24B illustrate an alternate embodiment of the trocar. Trocar 380 is similar to trocar 300 except for an elongated oval entrance opening 382 to lumen 383 for the guidewire and a beveled tip 384 to facilitate tunneling through tissue. The handle configuration 386 is also slightly different.

One method of use of the catheter will now be described in conjunction with FIGS. 25 to 28. The method will be described for inserting catheter 10, however it should be appreciated that any of the aforedescribed catheters can be inserted in the same manner.

First, needle "N" is inserted into the internal jugular vein to properly locate the vessel and a guidewire 20 is inserted through the needle so the distal tip of the guidewire extends unexposed into the right internal jugular vein "a" and into the superior vena cava "b" as shown in FIG. 25, not penetrating tissue. The guidewire 20 is further advanced into the right atrium "c". The needle "N" is then withdrawn, leaving the guidewire 20 in place, extending out of the patient's body at the proximal end portion 21 and the distal tip remaining unexposed in the vein during catheter insertion described below.

An exposed proximal end portion of the guide member extending outside the patient is passed through a subcutaneous tissue tunnel in a proximal direction so a proximal end portion extends through the tunnel. This is described below with reference to use of a trocar.

Figure 28A:
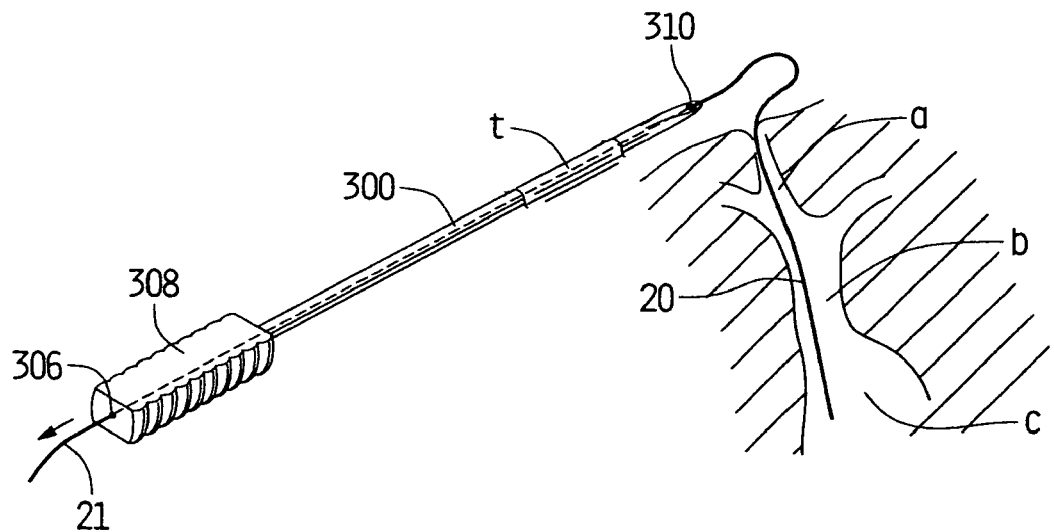
FIG. 28A illustrates the guidewire being threaded through the lumen of the trocar of FIG. 22.
Figure 28B:
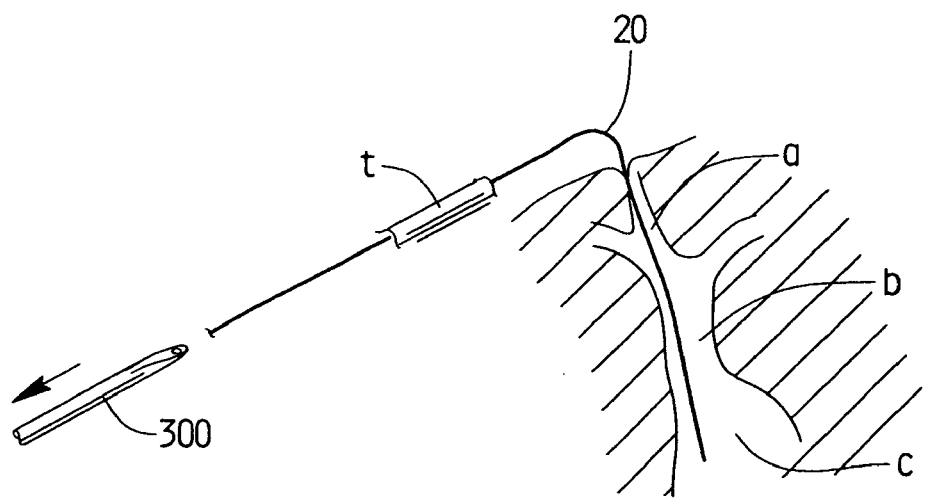
FIG. 28B illustrates the trocar being removed, leaving the guidewire in place extending through the tissue tunnel.

Next, trocar 300 is inserted through a first incision "s" in the patient, bluntly dissecting and tunneling under the skin, and forced out of the tissue at a second incision or site "u", creating a subcutaneous tunnel "t" under the tissue as shown in FIG. 27. This provides a way to secure the catheter as described below. Guidewire 20 is then threaded through lumen 304 of the trocar, with proximal portion 21 first inserted through trocar distal opening 310 so it emerges out of proximal opening 306 as shown in FIG. 28A. Trocar 300 is then withdrawn from the body in the direction of the arrow of FIG. 28B, leaving the guidewire 20 in place as shown. Thus, guidewire 20 extends from the right atrium and superior vena cava, out through the right internal jugular vein and through the tissue tunnel "t".

Catheter 10 is then threaded over the guidewire 20, (in a direction toward the distal tip of the guide member), acting as a guide member for the catheter with the exposed proximal end portion 21 of the guidewire 21 inserted through the distal tip lumen of the catheter, through the length of the central lumen, and through the hub 12 into the inflow tube 16 and out through fitting 15. The catheter 10 is thus threaded over the wire, through the tissue tunnel "t" where cuff 36 (not shown in FIG. 28C) is positioned in the tissue tunnel "t" to aid in securement of the catheter by enabling tissue ingrowth over a period of time. The catheter 10 is further advanced over guidewire 20 down into the right internal jugular vein, into the superior vena cava, and into the right atrium. The guidewire 20 is withdrawn in the direction of the arrow, leaving the catheter 10 in place for use as shown in FIG. 28C. Note the stiffening member 80 or 90 (not shown in FIG. 28C for clarity) is preferably utilized, i.e. inserted over the guidewire 20 through the fitting 15, inflow tube 16, hub 12, and central lumen 40 to help guide the catheter 10 as described in detail above.

As can be appreciated, the catheter will be inserted in a similar fashion through the left internal jugular vein to be positioned as depicted in FIG. 2. In this method, the subcutaneous tissue tunnel will be formed on the left side as shown (FIG. 2), by the trocar 300, and the catheter inserted over the guidewire through the subcutaneous tissue tunnel and through the left internal jugular vein and into the superior vena cava and right atrium in the same way as described for right side insertion. It should be understood that any of the aforedescribed catheters of the present invention can be inserted in this fashion.

An alternative method of insertion is illustrated in FIGS. 29A-29G. In this method instead of forming a second incision site adjacent the incision site through which the needle and guidewire are introduced into the internal jugular vein as in FIG. 27, the trocar 300 emerges from the needle/guidewire insertion site. Although catheter 10 is shown, any of the foregoing catheters can be inserted in the same manner.

In this method, the needle and guidewire are inserted in an identical manner as illustrated in FIGS. 25 and 26. After removal of the needle, the guidewire 20 is left in place extending outwardly from the incision site, designated by "w". Next, as shown in FIG. 29A, trocar 300 is inserted through a first incision (as in FIG. 27) to create a subcutaneous tissue tunnel; however, unlike FIG. 27, trocar 300 does not emerge at a second incision site "u". Instead, trocar 300 is advanced subcutaneously to the needle incision site "w", and emerges through the site "w" as shown. Thus, as shown in FIG. 29A, the distal end of trocar 300' exits incision site "w" alongside the guidewire 20.

Guidewire 20 is then inserted (threaded) through the opening in trocar 300 as described above and then the trocar is withdrawn through the tissue tunnel "t" and out through the first incision "s", pulling the guidewire 20 through the tunnel. After the guidewire 21 is pulled through the tunnel "t" and out through incision "s" the trocar 300 is removed as shown in FIG. 29B, leaving the guidewire 20 in place. Note the guidewire 20 is positioned to form a guidewire loop 22 outside the patient to facilitate the insertion of the catheter as will be described below.

The catheter 10 is then advanced over the guidewire 20 (FIG. 29C), through the tissue tunnel, and exiting incision site "w" into the internal jugular vein "a" (FIG. 29D). The catheter 10, as shown, is formed into a loop 13, tracking the loop 22 of guidewire 20, and then advanced downwardly through the internal jugular vein, the superior vena cava and into the right atrium. (FIG. 29E). The guidewire 20 is then withdrawn as shown in FIG. 29F, and the catheter 10 is pushed downwardly and/or pulled back to straighten the loop to position the catheter as shown in FIG. 29G.

It should be appreciated that formation of the loop in the guidewire and the catheter is optional and the procedure can be performed without the loop.

FIG. 30 shows an alternate embodiment of a trocar utilized to retrieve the suture and retract it through the subcutaneous tissue tunnel. Trocar 300' is similar to trocar 300 of FIG. 29 e.g. having a proximal opening 306' in handle 308', except for the provision of eyelet 312. The suture is threaded through the eyelet (shown as two small opposing holes in the wall at the distal end of the trocar 300') and the trocar is pulled proximally through the tissue tunnel to pull the suture out through incision "s". As shown, the trocar extends through incision "w", the same incision created for insertion of the needle and guidewire.

It should be understood that instead of an eyelet, a hook or other means can be provided on the trocar for holding the guidewire to enable pulling the guidewire through the tissue tunnel. That is, in these versions, the guidewire is not threaded through the trocar lumen, but rather the trocar is utilized to pull (retract) the guidewire through the tissue tunnel.

FIG. 21 illustrates an alternative trocar used for a different approach to catheter insertion. This trocar, designated by reference numeral 350, does not provide for an entire over the wire system, however it is used with an approach providing a partial over the wire system which eliminates the need for a tear way introducer sheath. As discussed in the Background Section of this application, tear away introducer sheaths are currently being utilized to guide the dialysis catheter through the vessels into the right atrium. To avoid the problems associated with the tear away sheath, the catheter in this alternate method, can be advanced over a guidewire which can be placed in the manner illustrated in FIGS. 25 and 26.

In this method, trocar 350 is attached to the distal end of the catheter by insertion of barbed end 352 into a mating fitting. Other means for temporarily attaching the trocar are also contemplated.

Trocar 350 has a blunt distal tip 354 and is advanced through a first tissue incision and out through a second tissue incision, bluntly dissecting tissue and forming a subcutaneous tissue tunnel in a similar manner as described above, except without the guidewire. Since trocar 350 is attached to the catheter, it pulls the catheter through the tissue tunnel, so it emerges out through the second incision. The trocar 350 is then detached from the catheter. The catheter is then bent as necessary and threaded over the guidewire into jugular vein, superior vena cava, and right atrium.

Turning now to one method of manufacturing the hub of the catheter, and with particular reference to FIGS. 31-37, a method is disclosed which enables connection of the central arterial (delivery) lumen of the catheter with an inflow tube and fluid connection of the five independent venous (withdrawal) lumens with a single outflow tube to provide fluid connection through the connectors.

Turning first to FIG. 31, a longitudinal slit 201 is formed at a proximal portion of catheter tube 203. FIG. 32 shows the relationship of the slit 201 and the central arterial lumen 205 as the slit is formed to communicate with the central lumen 205. As can be appreciated from the cross-sectional view of FIG. 33, the slit 201 is formed in the wall 206 of the catheter tube 203 between adjacent venous (withdrawal) lumens 209a-209e. Next, a metal pin 207 is inserted through the slit 201 for the molding process. Outer plastic inflow tubing 210 is placed over the metal pin 207 as shown in FIG. 35 to ultimately communicate with the central lumen 205. Outer plastic outflow tubing 211 is also shown positioned over the catheter tube 203 which will communicate with the venous lumens 209.

Next, conventional injection molding techniques are utilized so the soft plastic material flows around the catheter tube 203 and the metal pin 207 as shown in FIG. 36. Then, the material is cooled to harden, forming a hub 208, with the metal pin 207 removed to form lumen 204. Lumen 204 has a narrowed region 202. As shown in FIG. 37, lumen 204 fluidly connects lumen 207 of inflow tube 210 with the central lumen 205 of the catheter. Lumen 212 of outflow tubing 211 communicates with the five independent venous lumens 209.

FIGS. 38-39 illustrate another method for manufacturing the catheter connections. In this method, catheter body 402 of catheter 400 is separated into five segments 401a-401e at its proximalmost end, corresponding to each of the venous (withdrawal) lumens 403a-403e. FIG. 40 illustrates the five cuts 408 made in the catheter wall 407 between the adjacent venous lumens 403 to form the five segments 401.

A separate outflow connector tube 412a-412e is positioned within a respective venous lumen 403a-403e and is connected to a respective segment 401a-401e by solvent bonding or pressure fit. The proximal end of each connector tube 412 is positioned within outflow tube 414 which transports blood to the dialysis machine. Thus, blood flows through the venous lumens 403, through each outflow connector tube 401 and into a single outflow tube 414.

Inflow tubing 416 is connected to central arterial lumen by inflow connector tube 410 which is attached inside the arterial lumen by solvent bonding or pressure fit. Note that inflow connector tube 410 is positioned between the segments 401. It should be understood, that if fewer or larger number of venous lumens are provided, then an equal amount of outflow tubes would be utilized as the venous lumens would be cut into the corresponding number of segments.

FIGS. 41-43 illustrate another alternate method for manufacturing the hub of the catheter of the present invention. This hub and associated tubing is illustrated for use with a catheter having the lumen configuration of FIG. 9C, although it can be utilized with other lumen configurations as well.

A central lumen connector (intermediate) tube 702 is joined with central lumen 78 of catheter 700. Four venous connecting (intermediate) tubes 704 are connected to a respective venous lumen 76a. These tubes each have a lumen that is substantially circular in cross-section along its length. The substantially circular lumens corresponds to the cross-sectional shape of the venous lumens within catheter 10 which transition from a substantially oval cross-sectional configuration to a substantially circular cross-sectional configuration at the flared proximal portion shown in FIG. 43. Note that arterial lumen 78 also transitions to a substantially circular cross-sectional configuration.

Each of the connector tubes 704 is connected to multi-lumen extension (outflow) tube 708 which provides outflow of blood to the dialysis machine. Extension tube 708 has a flared distal portion 711 with four lumens 710, each configured for communicating with one of the connector tubes 704. As shown, each of the lumens 710 has a substantially circular cross-sectional configuration that transitions to a substantially triangular cross-sectional configuration towards the proximal portion.

Single lumen extension (inflow) tube 712, which provides inflow of blood to the patient, connects to connector tube 702. Tube 712 has a tapered distal end 718 and its lumen 719 transitions from a substantially circular cross-sectional configuration to a substantially square configuration toward the proximal end. Molding of housing 716 with the foregoing tubes forms the catheter hub. Conventional tube clamps, such as clamps 17,19 of FIG. 1, are placed around tubes 708, 712 for cutting off blood flow.

A rotatable suture ring 720 is placed around the catheter hub and preferably has a planar surface 722 to sit substantially flush with the patient's skin. Suture holes 724 are configured to receive sutures for attaching the ring (and thus the catheter) to the patient.

The catheters described above can optionally include a surface treatment on the exterior and/or the interior. The surface treatments can include for example, an hydrophilic coating to increase lubricity and facilitate insertion, a drug coating such as heparin or containing IIb, IIIa inhibitors, inert coating substances such as Sorins carbon coating, and/or active coatings such as a silver ion coating.

It should be appreciated that although the catheter is described herein as a dialysis catheter for hemodialysis, the catheter disclosed herein could have other surgical applications, such as drug delivery or blood sampling. Moreover, features of the catheter, tip configurations and lumen configurations can be utilized on other catheters.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A method of inserting a dialysis catheter into a right atrium of a patient comprising:
   providing a dialysis catheter having a first lumen for blood flow and a second lumen for blood flow, a terminal end of the first and second lumens being axially spaced;
   providing a first guidewire having a proximal end portion and a distal tip;
   inserting the first guidewire into the inferior vena cava of the patient so the distal tip remains in the vena cava and a proximal end portion extends out of the patient;
   passing the guidewire through a subcutaneous tissue tunnel by passing an exposed proximal end portion of the guidewire through the tunnel in a proximal direction;
   inserting a stiffening member through the first lumen in the catheter to advance the catheter over the guidewire;
   advancing the dialysis catheter and stiffening member over the guidewire into the vein and into the right atrium of the patient; and
   removing the guidewire leaving the dialysis catheter in place for a period of time.

2. The method of claim 1, wherein the step of inserting the stiffening member comprises the step of inserting the stiffening member such that a dilating distal tip of the stiffening member extends distally of the catheter.

3. The method of claim 2, further comprising the step of advancing the dialysis catheter subcutaneously over the guidewire through a tissue tunnel prior to the step of advancing the dialysis catheter into the vein.

4. The method of claim 1, wherein the guidewire is initially inserted through a needle.

5. A method of inserting a catheter into a patient comprising:
   creating a subcutaneous tissue tunnel;
   providing a guide member having a proximal end portion and a distal tip;
   inserting a guide member so the distal tip extends into and is positioned unexposed in the vein of the patient and an exposed proximal end portion extends outside of the patient;
   providing a catheter having a first lumen for blood delivery and a second lumen for blood withdrawal;

after the step of inserting the guide member, passing the guide member in a proximal direction so the proximal end portion extends through the subcutaneous tissue tunnel; and inserting the catheter into the vein of the patient over the guide member in a direction toward the distal tip of the guide member with the distal tip remaining unexposed in the vein during insertion.

6. The method of claim 5, further comprising the step of inserting into the catheter a stiffening member having a lumen so the stiffening member is inserted into the vein of the patient over the guide member.

7. The method of claim 6, further comprising the steps of removing the guide member and leaving the catheter in position extending through the subcutaneous tissue tunnel and vein to enable blood delivery to the patient through the first lumen and blood withdrawal from the patient through the second lumen to treat the patient's blood, the step of leaving the catheter in place further comprises the step of enabling blood withdrawal through at least one withdrawal opening in the catheter and enabling blood delivery through at least one opening in a distal portion of the catheter axially spaced from the withdrawal opening.

8. The method of claim 6, wherein the step of inserting the stiffening member includes the steps of securing the stiffening member to a proximal portion of the catheter.

9. The method of claim 6, wherein the step of inserting the stiffening member includes the step of inserting the stiffening member through the blood delivery lumen of the catheter.

10. The method of claim 6, wherein the step of inserting the stiffening member comprises the step of inserting the stiffening member such that a dilating distal tip of the stiffening member extends distally of the catheter.

11. The method of claim 5 wherein the step of inserting the catheter over the guide member includes the guide member extending through one of the lumens in the catheter.

12. The method of claim 5, further comprising the step of forming a loop in the catheter prior to full insertion of the catheter into the vein of the patient.

13. The method of claim 5, wherein the guide member is initially inserted through a needle.

14. A method of inserting a catheter into a patient without the use of a tear away sheath comprising:

providing a catheter;

inserting a guide member through the incision into the vein of a patient so a distal tip of the guide member extends into and is positioned unexposed in the vein of the patient and an exposed proximal end portion extends outside of the patient;

creating a subcutaneous tissue tunnel;

providing an insert member;

inserting the insert member into the catheter;

passing an exposed portion of the guide member through the subcutaneous tissue tunnel;

inserting, without the use of a tear away sheath, the insert member and catheter into the vein of the patient over the guide member in a direction toward the distal tip of the guide member as the guide member extends through an opening in the insert member and the distal tip remains unexposed in the vein during insertion; and securing the catheter to the patient.

15. The method of claim 14, further comprising the step of securing the insert member to the catheter.

16. The method of claim 14, wherein the step of passing the guide member through the subcutaneous tissue tunnel comprises the step of providing a trocar and inserting the guide member through an opening in the trocar.

17. A method of inserting a catheter into a vein of a patient comprising:

inserting a guidewire into the vein of a patient, the guidewire extending out of and incision to form a loop outside the patient;

creating a subcutaneous tissue tunnel;

inserting a catheter through a first end of the subcutaneous tissue tunnel to exit a second end of the tunnel;

inserting the catheter over the loop in the guidewire and into the vein of the patient, the step of inserting including the step of providing a stiffening member within the catheter having an opening to pass over the guidewire as it is advanced into the vein with the catheter; and securing the catheter to the patient.

18. The method of claim 17, further comprising the step of securing the stiffening member to the catheter.

19. The method of claim 17, wherein the step of providing a stiffening member within the catheter includes the step of placing the stiffening member within a lumen of the catheter.

20. The method of claim 17, further comprising the step of inserting the catheter into the patient is performed without inserting the catheter through a tear away sheath.

21. The method of claim 17, wherein the guidewire is initially inserted through a needle.

* * * * *